United States Patent
Isales et al.

(10) Patent No.: US 6,410,508 B1
(45) Date of Patent: Jun. 25, 2002

(54) GLUCOSE-DEPENDENT INSULINOTROPIC PEPTIDE FOR USE AS AN OSTEOTROPIC HORMONE

(76) Inventors: Carlos M. Isales, 3413 Woodstone Pl., Augusta, GA (US) 30909; Roni J. Bollag, 231 Watervale Rd., Martinez, GA (US) 30907; Howard Rasmussen, 820 Barrett La., Augusta, GA (US) 30909

( * ) Notice: Subject to any disclaimer, the term of this patent is extended or adjusted under 35 U.S.C. 154(b) by 0 days.

(21) Appl. No.: 09/414,189

(22) Filed: Oct. 7, 1999

Related U.S. Application Data

(60) Provisional application No. 60/103,495, filed on Oct. 8, 1998, and provisional application No. 60/103,333, filed on Oct. 7, 1998.

(51) Int. Cl.$^7$ .......................... A01N 37/18; A61K 38/28; A61K 39/00; C12N 21/06; C12N 1/00; C12N 5/00

(52) U.S. Cl. ................. 514/2; 514/3; 514/12; 530/303; 530/308; 424/184.1; 424/198.1; 435/69.1; 435/325; 435/243

(58) Field of Search .................... 514/2, 3, 12, 866; 530/303, 308; 424/184.1, 198.1; 435/69.1, 69.4, 325, 243

(56) References Cited

U.S. PATENT DOCUMENTS

| | | |
|---|---|---|
| 3,625,214 A | 12/1971 | Higuchi |
| 4,244,946 A | 1/1981 | Rivier et al. |
| 4,305,872 A | 12/1981 | Johnston et al. |
| 4,316,891 A | 2/1982 | Guillemin et al. |
| 4,629,784 A | 12/1986 | Stammer |
| 4,792,525 A | 12/1988 | Ruoslahti et al. |
| 4,868,116 A | 9/1989 | Morgan et al. |
| 4,906,474 A | 3/1990 | Langer et al. |
| 4,925,673 A | 5/1990 | Steiner et al. |
| 4,980,286 A | 12/1990 | Morgan et al. |

FOREIGN PATENT DOCUMENTS

| | | |
|---|---|---|
| EP | 0 269 072 A2 | 6/1988 |
| EP | 0 479 210 A2 | 4/1992 |
| WO | WO 93/01286 A2 | 1/1993 |
| WO | WO 98/24464 A1 | 6/1998 |

OTHER PUBLICATIONS

Kundu et al, Peptides 20:523–537, 1999.*
Ziegler et al, Steroids 63:344–348, 1998.*
Bollag et al, Endocrinology, 141(3):1228–35, 2000.*
Rosenberg et al., Gene Therapists, Heal Thyself, Mar. 2000, Science, vol. 287 p. 1751.*
Verma, Gene Therapy: Beyond 2000, Jun. 2000, Molecular Therapy, vol. 1 No. 6 p. 493.*
Verma et al., Gene therapy–promises, problems and prospects, Sep. 1997, Nature, vol. 389 pp. 239–242.*
Anderson, Human gene therapy, Apr. 1998, Nature, vol. 392 pp. 25–30.*
Touchett, Gene therapy: Not ready for prime time, Jan. 1996, Nature Medicine, vol. 2 No. 1 pp. 7–8.*
Bollag, et al., "Glucose–dependent insulinotropic peptide has anabolic effects of osteoblastic–like cells," *J. Bone Min. Res.* 14:S345 (1999).
Tseng, et al., "Glucose–dependent insulinotropic peptide structure of the precursor and tissue–specific expression in rat," *Proc. Natl. Acad. Sci. USA* 90:1992–1996 (1993).
Abou–Samra, et al., "Expression cloning of a common receptor for parathyroid.hormone and parathyroid hormone–related peptide from rat osteoblast–like cells: a single receptor stimulates intracellular accumulation of both cAMP and inositol trisphosphates and increases intracellular free calcium," *Proc Natl Acad Sci U S A* 89(7):2732–6 (1992).
Agrawal, et al., "Oligodeoxynucleoside phosphoroamidates and phosphorothioates as inhibitors of human immunodeficiency virus," *Proc. Natl. Acad. Sci. USA* 85(19):7079–7083 (1988).
Amizuka, et al., "Programmed cell death of chondrocytes and aberrant chondrogenesis in mice homozygous for parathyroid hormone–related peptide gene deletion," *Endocrinology.* 137(11):5055–67 (1996).
Arjmandi, et al., "Dietary soybean protein prevents bone loss in an ovariectomized rat model of osteoporosis," *J Nutr.* 126(1):161–7 (1996).
Askew, et al., "Molecular Recognition with Convergent Functional Groups, 6, Synthetic and Structural Studies with a Model Receptor for Nucleic Acid Components," *J. Am. Chem. Soc.,* 111:1082–1090 (1989).

(List continued on next page.)

*Primary Examiner*—Scott D. Priebe
*Assistant Examiner*—Sumesh Kaushal
(74) *Attorney, Agent, or Firm*—Cynthia B. Rothschild, Esq; Kilpatrick Stockton LLP

(57) ABSTRACT

The examples demonstrate that GIP receptor mRNA and protein are present in normal bone and osteoblastic-like cell lines, and that high-affinity receptors for GIP can be demonstrated by $^{125}$I GIP binding studies. When applied to osteoblast-like cells (SaOS2), GIP stimulated an increase in cellular cAMP content and in intracellular calcium, with both responses being dose dependent. Moreover, administration of GIP results in elevated expression of collagen type I mRNA as well as an increase in alkaline phosphatase activity. Both of these effects reflect anabolic actions of presumptive osteoblasts. These results provide the first evidence that GIP receptors are present in bone and osteoblastic like cells and that GIP modulates the function of these cells. GIP has anabolic actions on remodeling bone, increasing vertebral bone density in a rat model of osteoporosis. GIP at 10 nM inhibits PTH-induced bone resorption in a fetal long bone assay and stimulates the synthesis of type 1 collagen mRNA. Transgenic mice overexpressing GIP have increased bone density compared to same age controls. GIP or analoges thereof can therefore be used as a therapeutic to inhibit bone resorption and to maintain or increase bone density. GIP antagonists, compounds which block binding to the GIP receptor, can be used to decrease bone density.

13 Claims, 13 Drawing Sheets-

OTHER PUBLICATIONS

Blume, et al., "Triple Helix Formation by Purine–rich Oligonucleotides Targeted to the Human Dihydrofolate Reductase Promoter." *Nucl. Acids Res.* 20:1777–1784 (1992).

Campos, et al., "Divergent tissue–specific and developmental expression of receptors for glucagon and glucagon–like peptide–1 in the mouse," *Endocrinology.* 134(5):2156–64 (1994).

Clackson, et al., "Making antibody fragments using phage display libraries," *Nature.* 352(6336):624–8 (1991).

Cooney, et al., "Site–Specific Oligonucleotide Binding Represses Transcription of the Human c–myc Gene in Vitro," *Science* 241:456–459 (1988).

Crooke, "Progress Toward Oligonucleotide Therapeutics: Pharmacodynamic Properties," *FASEB J.* 7:533–539 (1993).

Daugherty, et al., "Polymerase chain reaction facilitates the cloning, CDR–grafting, and rapid expression of a murine monoclonal antibody directed against the CD18 component of leukocyte integrins," *Nucleic Acids Res.* 19(9):2471–6 (1991).

Duval–Valentin, et al., "Specific Inhibition of Transcription by Triple Helix–Forming Oligonucleotides," *Proc. Natl. Acad. Sci. USA,* 89:504–508 (1992).

Fauchére, QSAR: Quantitative Structure–Activity Relationships in Drug Design (Alan R. Liss, inc. 1989).

Gasalla–Herraiz, et al., "Calcium–sensitive probes for the measurement of intracellular calcium: effects of buffer system and magnesium concentration," *Biochem Biophys Res Commun.* 214(2):373–88 (1995).

Goldring, et al., "Characterization of the structural and functional properties of cloned calcitonin receptor cDNAs," *Horm Metab Res.* 25(9):477–80 (1993).

Gregoriadis, "Liposomes", Drug Carriers in Biology and Medicine, Chapter 14, pp. 287–341, (Academic Press, 1979).

Grigoriev, et al., "A Triple Helix–forming Oligonucleotide–Intecalator Conjugate Acts as a Transcriptional Repressor via Inhibition of NF KB Binding to Interleukin–2 Receptor α–Regulatory Sequence," *J. Biol. Chem.* 267:3389–3395 (1992).

Higashimoto & Liddle, "Isolation and characterization of the gene encoding rat glucose–dependent insulinotropic peptide," *Biochem. Biophys. Res. Commun.* 193(1):182–190 (1993).

Isales, et al., "Parathyroid hormone modulates angiotensin II–induced aldosterone secretion from the adrenal glomerulosa cell," *Endocrinology.* 129(1):489–95 (1991).

Itakura, et al., "Synthesis and use of synthetic oligonucletides", in *Ann. Rev. Biochem.* 53:323–356 (1984).

Jubiz, et al., "Circadian rhythm in serum parathyroid hormone concentration in human subjects: correlation with serum calcium, phosphate, albumin, and growth hormone levels," *J. Clin Invest.* 51(8):2040–6 (1972).

Kabat, et al., *Sequences of Proteins of Immunological Interest,* 4th Ed. (U.S. Dept. Health and Human Services, Bethesda, MD, 1987).

Knapper, et al., "Nutrient–induced secretion and metabolic effects of glucose–dependent insulinotropic polypeptide and glucagon–like peptide–1," *Proc Nutr Soc.* 55(1B):291–305 (1996).

Lee, et al., "Parathyroid hormone–related peptide delays terminal differentiation of chondrocytes during endochondral bone development," *Endocrinology.* 137(11):5109–18 (1996).

Lewis & Dean, "Automated site–directed drug design: the concept of spacer skeletons for primary structure generation," *Proc. R. Soc. Lond.,* 236(1283):125–140 (1989).

Lewis & Dean, "Automated site–directed drug design: the formation of molecular templates in primary structure generation," *Proc. R. Soc. Lond.,* 236(1283):141–162 (1989).

Maher, et al., "Inhibition of DNA binding proteins by oligonucleotide–directed triple helix formation," *Science* 245:725–730 (1989).

McKinlay & Rossmann, "Rational Design of Antiviral Agents," *Annual Review of Pharmacology and Toxicology,* 29:111–122 (1989).

Merrifield, "Sold–Phase Peptide Synthesis. I. The Synthesis of a Tetrapeptide," *J. Am. Chem. Soc.* 85:2149–2154 (1964).

Mulligan, "The Basic Science of Gene Therapy", *Science* 260:926–932 (1993).

Narang, et al., "Chemical Synthesis of Deoxyoligonucleotides by the Modified Triester Method," in *Methods Enzymol.* 65:610–620 (1980).

Offensperger, et al., "In Vivo inhibition of duck hepatitis B virus replication and gene expression by phosphorothioate modified antisense oligodeoxynucleotides," *EMBO J.* 12(3):1257–1262 (1993).

Onyia, et al., "Parathyroid hormone (1–34)–mediated interleukin–6 induction," *J Cell Biochem* 67(2):265–74 (1997).

Orloff, et al., "A midregion parathyroid hormone–related peptide mobilizes cytosolic calcium and stimulates formation of inositol trisphosphate in a squamous carcinoma cell line," *Endocrinology.* 137(12):5376–85 (1996).

Orson, et al., "Oligonucleotide inhibition of IL2Rα mRNA transcription by promoter region collinear triplex formation in lymphocytes", *Nucl. Acids Res.* 19:3435–3441 (1991).

Pederson & Brown, "The insulinotropic action of gastric inhibitory polypeptide in the perfused isolated rat pancreas," *Endocrinology.* 99(3):780–5 (1976).

Pollock, et al., "In vivo demonstration that parathyroid hormone and parathyroid hormone–related protein stimulate expression by osteoblasts of interleukin–6 and leukemia inhibitory factor," *J Bone Miner Res.* 11(6):754–9 (1996).

Postel, et al., "Evidence that a triplex–forming oligodeoxyribonucleotide binds to the c–myc promoter in HeLa cells, thereby reducing c–myc mRNA levels", *Proc. Natl. Acad. Sci. USA* 88:8227–8231 (1991).

Ripka, "Computers Picture the Perfect Drug," *New Scientist,* 54–57 (Jun. 16, 1988).

Rouvinen, et al., "Computer–Aided Drug Design," *Acta Pharmaceutica Fennica,* 97:159–166 (1988).

Sambrook et al., *Molecular Cloning: A Laboratory Manual,* Second Edition, Cold Spring Harbor Laboratory Press:Cold Spring Harbor, N.Y., 1989.

Sarin, et al., "Inhibition of acquired immunodeficiency syndrome virus by oligodeoxynucleoside methylphosphonates," *Proc. Natl. Acad. Sci. USA* 85(20):7448–7794 (1989).

Shaw, et al., "Modified deoxyoligonucleotides stable to exonuclease degradation in serum," *Nucleic Acids Res.* 19(4):747–750 (1991).

Szostak, "In vitro genetics," *TIBS* 19:89–93 (1992).

Usdin, et al., "Gastric inhibitory polypeptide receptor, a member of the secretin–vasoactive intestinal peptide receptor family, is widely distributed in peripheral organs and the brain," *Endocrinology.* 133(6):2861–70 (1993).

Wickstrom, et al., "Human promyelocytic leukemia HL–60 cell proliferation and c–myc protein expression are inhibited by an antisense pentadecadeoxynucleotide targeted against c–myc mRNA", *Proc. Natl. Acad. Sci. USA* 85:1028–1032 (1988).

Young, et al., "Triple helix formation inhibits transcription elongation in vitro", *Proc. Natl. Acad. Sci. USA* 88:10023–10026 (1991).

Zamecnik, et al., "Inhibition of Rous sarcoma virus replication and cell transformation by a specific oligodeoxynucleotide," *Proc. Natl. Acad. Sci. USA* 75:280–284 (1978).

Zamecnik, et al., "Inhibition of replication and expression of human T–cell lymphotropic virus type III in cultured cells by exogenous systhenic oligonucleotides complementary to viral RNA," *Proc. Natl. Acad. Sci.* 83:4143–4146 (1986).

Zhu, et al., "Systemic Gene Expression After Intravenous DNA Delivery into Adult Mice," *Science* 261:209–211 (1993).

* cited by examiner

SEQUENCE LISTING

<160> NUMBER OF SEQ ID NOS: 1

<210> SEQ ID NO 1
<211> LENGTH: 445
<212> TYPE: PRT
<213> ORGANISM: Homo sapiens
<220> FEATURE:
<223> OTHER INFORMATION: From 6-25 synthetic ol igopeptide region used to make antibodies blocking GIP recept or activation

<400> SEQUENCE: 1

```
Arg Ala Glu Thr Gly Ser Lys Gly Gln Thr A la Gly Glu Leu Tyr Gln
 1               5                  10                  15

Arg Trp Glu Arg Tyr Arg Glu Cys Gln G lu Thr Leu Ala Ala
            20                  25                  30

Glu Pro Pro Ser Gly Leu Ala Cys Asn Gly S er Phe Asp Met Tyr Val
            35                  40                  45

Cys Trp Asp Tyr Ala Ala Pro Asn Ala Thr A la Arg Ala Ser Cys Pro
 50                  55                  60

Trp Tyr Leu Pro Trp His His Val Ala A la Gly Phe Val Leu Arg
 65                  70                  75                  80

Gln Cys Gly Ser Asp Gly Gln Trp Gly Leu T rp Arg Asp His Thr Gln
            85                  90                  95

Cys Glu Asn Pro Glu Lys Asn Glu Ala Phe L eu Asp Gln Arg Leu Ile
            100                 105                 110

Leu Glu Arg Leu Gln Val Met Tyr Thr Val G ly Tyr Ser Leu Ser Leu
            115                 120                 125

Ala Thr Leu Leu Leu Ala Leu Leu Ile Leu S er Leu Phe Arg Arg Leu
 130                 135                 140

His Cys Thr Arg Asn Tyr Ile His Ile Asn L eu Phe Thr Ser Phe Met
 145                 150                 155                 160

Leu Arg Ala Ala Ala Ile Leu Ser Arg Asp A rg Leu Leu Pro Arg Pro
            165                 170                 175

Gly Pro Tyr Leu Gly Asp Gln Ala Leu Ala L eu Trp Asn Gln Ala Leu
            180                 185                 190

Ala Ala Cys Arg Thr Ala Gln Ile Val Thr G ln Tyr Cys Val Gly Ala
            195                 200                 205

Asn Tyr Thr Trp Leu Leu Val Glu Gly Val T yr Leu His Ser Leu Leu
 210                 215                 220

Val Leu Val Gly Gly Ser Glu Glu Gly His P he Arg Tyr Leu Leu
 225                 230                 235                 240

Leu Gly Trp Gly Ala Pro Ala Leu Phe Val I le Pro Trp Val Ile Val
            245                 250                 255

Arg Tyr Leu Tyr Glu Asn Thr Gln Cys Trp G lu Arg Asn Glu Val Lys
            260                 265                 270

Ala Ile Trp Trp Ile Ile Arg Thr Pro Ile L eu Met Thr Ile Leu Ile
            275                 280                 285

Asn Phe Leu Ile Phe Ile Arg Ile Leu Gly I le Leu Leu Ser Lys Leu
            290                 295                 300

Arg Thr Arg Gln Met Arg Cys Arg Asp Tyr A rg Leu Arg Leu Ala Arg
 305                 310                 315                 320

Ser Thr Leu Thr Leu Val Pro Leu Leu Gly V al His Glu Val Val Phe
            325                 330                 335

Ala Pro Val Thr Glu Glu Gln Ala Arg Gly A la Leu Arg Phe Ala Lys
```

-continued

```
                    340                 345                 350
Leu Gly Phe Glu Ile Phe Leu Ser Ser Phe Gln Gly Phe Leu Val Ser
        355                 360                 365
Val Leu Tyr Cys Phe Ile Asn Lys Glu Val Gln Ser Glu Ile Arg Arg
    370                 375                 380
Gly Trp His His Cys Arg Leu Arg Arg Ser Leu Glu Glu Gln Arg
385             390                 395                 400
Gln Leu Pro Glu Arg Ala Phe Arg Ala Leu Pro Ser Gly Ser Gly Pro
                405                 410                 415
Gly Glu Val Pro Thr Ser Arg Gly Leu Ser Ser Gly Thr Leu Pro Gly
            420                 425                 430
Pro Gly Asn Glu Ala Ser Arg Glu Leu Glu Ser Tyr Cys
        435                 440                 445
```

GLUCOSE-DEPENDENT INSULINOTROPIC PEPTIDE FOR USE AS AN OSTEOTROPIC HORMONE This application claims priority to U.S. Provisional Applications Ser. Nos. 60/103,333 filed Oct. 7, 1998, and 60/103,495 filed Oct. 8, 1998.

BACKGROUND OF THE INVENTION

The United States government has rights in this invention by virtue of NIH grants DK-19813 and HD 34149 and Yale Core Center for Musculoskeletal Disorders P30 AR46032.

Glucose-dependent Insulinotropic Peptide (GIP) is a 42 amino acid peptide synthesized and secreted from endocrine cells in the small intestine. GIP's role in coupling nutrient intake and insulin secretion, the "incretin" effect, is well known. Parathyroid hormone and vitamin D are known to couple calcium intake to bone formation but no coupling hormone has been identified for nutrient intake and bone formation.

GIP is secreted from enteric endocrine cells in the proximal small intestine, whereas glucagon-like peptide 1 (GLP-1, another major "incretin" hormone) is secreted from endocrine cells in the terminal small bowel. Until recently, the glucose-dependent insulinotropic peptide (GIP) had been considered a parochial hormone of the enteric endocrine system with its major site of action being the β-cells of the endocrine pancreas. R. A. Pederson, et al., *Endocrinology* 99, 780–785 (1976). However, the cloning of the GIP receptor led to the discovery that the receptor is expressed in a wide range of tissues and organs, including the exocrine pancreas, and distal small cells in several vascular beds. T. B. Usdin, et al., *Endocrinology* 133,2861–2870 (1993).

This widespread receptor distribution suggests as yet undefined physiological actions of GIP. Most studies seeking to define the actions of GIP have focused on synergism between GIP and glucose in stimulating insulin secretion. GIP infusions have also been shown to inhibit effects of glucagon on the liver while enhancing those of insulin, and to have dual effects on hepatic blood flow, increasing flow through the portal vein and inhibiting flow through the hepatic artery. Ironically, the effect for which GIP was discovered, inhibition of gastric acid secretion, seems to be a minor pharmacological effect of little physiological significance.

At present the main modulator of bone metabolism is thought to be the PTH-Vitamin D axis. Parathyroid hormone is known to be negatively regulated by nutrient absorption, with PTH secretion decreasing after a calcium-rich meal and rising during fasting W. Jubiz, et al., *J Clin Invest* 51, 2040–2046 (1972). Receptors for PTH are found on osteoblasts and PTH-induces cytokine expression which in tun modulates osteoclastic activity, J. E. Onyia, et al., *J Cell Biochem* 67, 265–74 (1997), J. H. Pollock, et al., *J Bone Miner Res* 11, 754–9 (1996). Thus, PTH-induced bone turnover is generally a coupled process and, in conjunction with Vitamin D, PTH plays a major role in bone mineralization.

In addition to calcium intake, however, bone depends for its growth and remodeling on nutrient intake. In fact, even in a state of high bone turnover, such as in an ovariectomized rat, it is possible to prevent bone loss by altering the rat's diet and placing her on a specified protein diet, B. H. Arjmandi, et al., *J Nutr* 126, 161–167 (1996), suggesting that a gut-induced signal may modulate bone turnover. To date, the hormones of the enteric endocrine system have not been considered to play a major role in coordinating nutrient intake with skeletal growth and remodeling.

It is therefore an object of the present invention to provide a means for regulating skeletal growth and remodeling.

It is a further object of the present invention to provide therapeutic formulations for treatment of disorders such as osteoporosis.

SUMMARY OF THE INVENTION

The examples demonstrate that GIP receptor mRNA and protein are present in normal bone and osteoblastic-like cell lines, and that high-affinity receptors for GIP can be demonstrated by $^{125}I$ GIP binding studies. When applied to osteoblast-like cells (SaOS2), GIP stimulated an increase in cellular cAMP content and in intracellular calcium, with both responses being dose dependent. Moreover, administration of GIP results in elevated expression of collagen type I mRNA as well as an increase in alkaline phosphatase activity. Both of these effects reflect anabolic actions of presumptive osteoblasts. These results provide the first evidence that GIP receptors are present in bone and osteoblastic like cells and that GIP modulates the function of these cells.

GIP has anabolic actions on remodeling bone, increasing vertebral bone density in a rat model of osteoporosis. GIP at 10 nM inhibits PTH-induced bone resorption in a fetal long bone assay and stimulates the synthesis of type 1 collagen mRNA. Transgenic mice overexpressing GIP have increased bone density compared to same age controls.

GIP or analoges thereof can therefore be used as a therapeutic to inhibit bone resorption and to maintain or increase bone density. GIP antagonists, compounds which block binding to the GIP receptor, can be used to decrease bone density.

BRIEF DESCRIPTION OF THE DRAWINGS

FIG. 1A shows that GIP increases $[Ca2).+]_i$ in a dose dependent manner in SaOS2 cells. SaOS2 cells were grown on glass coverslips and loaded with the fluorescent calcium sensitive probe fura-2 and stimulated with increasing doses of GIP. Peak increases in intracellular calcium from four different experiments were calculated. Data is expressed as mean±SEM; *=p<0.001; =p<0.001. FIG. 1B shows the results when SaOS2 cells were grown in six-well plates, preincubated with the phosphodiesterase inhibitor IBMX (0.5 mM -10 minutes), and stimulated with increasing doses of GIP (10 minutes). Cellular cAMP was measured with a commercially available radioimmunoassay (Biomedical Technologies, Stoughton, Mass.). Data is expressed as mean+SEM; =p<0.001.

FIG. 2B is a graph where SaOS2 cells were grown in T75 as above and stimulated with 1 nM GIP for the various time points as indicated (0, 3, 6, 9 and 12 hours), and subjected to northern analysis. The densitometry of four different experiments was summed and is expressed as a bar graph; *=p<0.001 vs control, as a function of time, in FIG. 2A.

DETAILED DESCRIPTION OF THE INVENTION

Figure 1A:
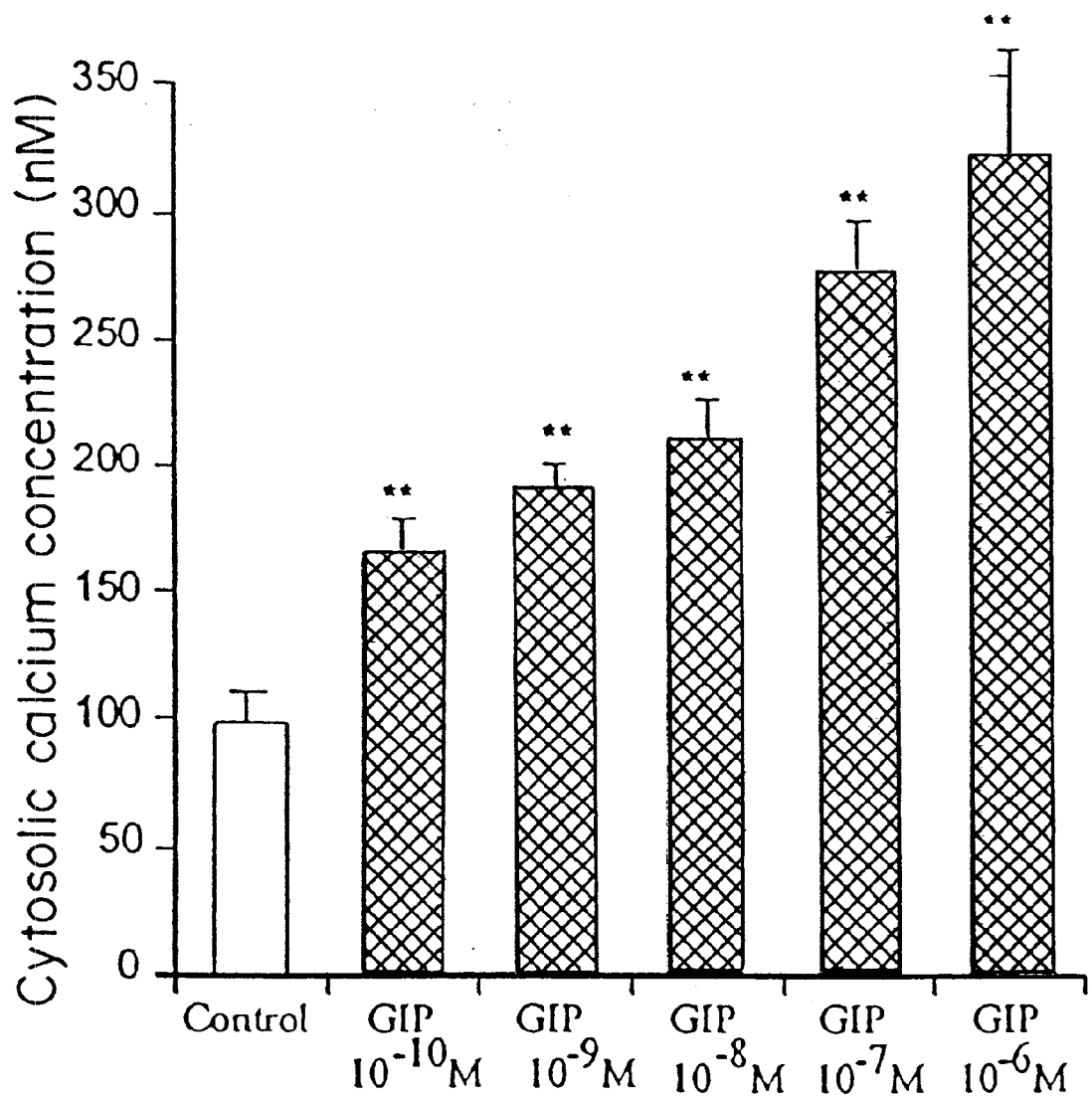
FIGS. 1A and 1B are graphs of the effect of GIP (0.1 nM to 1 micromolar GIP) on cytosolic calcium concentration (nM) (FIG. 1A) and cellular cAMP apg/ml) (FIG. 1B).

Based on the data in the following examples, relating to the role of GIP in bone remodeling, it is believed that PTH and GIP have complementary roles in the regulation of skeletal events. PTH plays a major role in stimulating the recruitment of mononuclear cells to become osteoclasts; and, once formed, of stimulating these osteoclasts to resorb bone. PTH may also increase the lifetime of the osteoclasts. In contrast, GIP acts to shift the remodeling units from their osteoclastic to their osteoblastic phase of activity by acting directly on osteoclasts. Once the cells of a remodeling unit are in the osteoblastic phase of activity, both PTH and GIP play unique roles in mediating this phase of bone formation: PTH by stimulating osteoblast proliferation, and GIP by stimulating the bone forming activities of these osteoblasts. A similar relationship between the actions of these two hormones also defines their roles in the regulation of bone growth at the epiphyseal plates: PTH by stimulating the proliferation of chondrocytes, and GIP, by stimulating these chondrocytes to produce the collagen matrix.

Despite their similarities, GIP and PTH receptors also show distinct differences. First, PTH, but not GIP, acts on osteoblasts to stimulate bone resorption. Second, receptors for both hormones are present on cells in the epiphyseal growth plate, but these receptors are expressed on different cell types: PTH receptors on the chondrocytes between the proliferative zone and hypertrophic zone, K. Lee, et al., *Endocrinology* 137, 5109–5118 (1996), N. Amizuka, et al., *Endocrinology* 137, 5055–67 (1996), and GIP receptors on the chondrocytes of the hypertrophic zone. This latter difference relates to another aspect of bone physiology. Under normal circumstances, PTH secretion is low during the day and increases during the night because the plasma $Ca^{2+}$ falls. W. Jubiz, et al., *J Clin Invest* 51, 2040–2046 (1972). GIP secretion is highest throughout the day as a result of food intake, and falls during the overnight fast. J. M. Knapper, et al., *Proc Nutr Soc* 55, 291–305 (1996).

It follows that GIP plays an important role in the regulation of both skeletal growth in the child, and skeletal remodeling in the adult. GIP receptors are present in bone-derived cells and stimulation of these cells with GIP leads to an increase in intracellular calcium concentration and cellular cAMP content, resulting in increased type I collagen synthesis and inhibition of PTH-stimulated bone resorption. The data presented in the examples supports GIP's role as an "incretin" hormone involves the bone in an "entero-osseous axis". As a result, GIP or its analogues or antagonists which bind to the receptor can be used to modulate bone deposition.

GIP Formulations

GIP

GIP can be isolated or more preferably prepared synthetically, either by chemical synthesis or through expression of recombinant GIP. The amino acid and nucleotide sequences were published by Higashimoto and Liddle, *Biochem. Biophys. Res. Commun.* 193(1), 182–190 (1993). As used herein, unless specifically stated otherwise, the term "GIP" refers to the human sequence, and degenerate variants thereof and their equivalents in other species of origin, as well as functionally equivalent variants, having additions, deletions, and substitutions of either nucleotides or amino acids which do not significantly alter the functional activity of the peptide.

In another embodiment, compounds which mimic, or antagonize, the action of GIP, or its receptor, can be used. As used herein, analogues are GIP, fragments or fusions of GIP, anit-idiotypic antibodies to GIP or fragments thereof which bind to the GIP receptor, or synthetic structural mimics, having equivalent activity to GIP. These are jointly referred to herein as GIP, unless otherwise specified. Antagonists will typically be similar types of compounds which block or compete for binding to the GIP receptor. These can be obtained using methods known to those skilled in the art, some of which are described below, and identified by screening methods such as those in the examples.

The receptor proteins are useful as targets for compounds which turn on, or off, or otherwise regulate binding to the GIP receptor, in a manner which mimics GIP function or antagonizes GIP function. The assays described below clearly provide routine methodology by which a compound can be tested for an inhibitory effect, or a stimulatory effect, on binding of a specific compound, to GIP or its receptor. The in vitro studies of compounds which appear to modify binding selectively are then confirmed by animal testing. Studies based on inhibition of binding are predictive for indirect effects, for example, on alteration of receptor binding. Assays for testing compounds for useful activity can be based solely on interaction with the receptor or GIP, on cells or in solution or immobilized on inert substrates.

Alternatively, the assays can be based on interaction with the gene sequence encoding GIP or the receptor protein, preferably the regulatory sequences directing expression of GIP or the receptor protein. For example, antisense which binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of receptor binding or GIP activity.

Random Generation of Receptor or Receptor Encoding Sequence Binding Molecules

Molecules with a given function, for example, catalytic or ligand- binding, can be selected for from a complex mixture of random molecules in what has been referred to as "in vitro genetics" (Szostak, TIBS 19:89, 1992). One synthesizes a large pool of molecules bearing random and defined sequences and subjects that complex mixture, for example, approximately $10^{15}$ individual sequences in 100 $\mu$g of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1990; Bock et al, 1992).

Computer Assisted Drug Design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159–166; Ripka, *New Scientist* 54–57 (Jun. 16, 1988); McKinlay and Rossmann, 1989 *Annu. Rev. Pharmacol. Toxiciol* 29, 111–122; Perry and Davies, QSAR: *Quantitative Structure-Activity Relationships in Drug Design* pp. 189–193 (Alan R. Liss, Inc. 1989); Lewis and Dean, 1989 *Proc. R. Soc. Lond.* 236, 125–140 and 141–162; and, with respect to a model receptor for nucleic acid components, Askew, et al., 1989 *J. Am. Chem. Soc.* 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified. Although described above with reference to design and generation of compounds which could alter binding, one could also screen libraries of known compounds, including natural products or synthetic chemicals, and biologically active materials, including proteins, for compounds which are inhibitors or activators.

Generation of Nucleic Acid Regulators

Nucleic acid molecules containing the 5' regulatory sequences of the receptor genes can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors enable the introduction of nucleic acid sequences in vivo (see, e.g., Mulligan, 1993 *Science*, 260, 926–932; U.S. Pat. No. 4,980, 286; U.S. Pat. No. 4,868,116; incorporated herein by reference). A number of delivery systems have been developed in which nucleic acid is encapsulated in cationic liposomes which can be injected intravenously into a mammal. This system has been used to introduce DNA into the cells of multiple tissues of adult mice, including endothelium and bone marrow (see, e.g., Zhu et al., 1993 *Science* 261, 209–211; incorporated herein by reference). The 5' flanking sequences of the receptor gene can also be used to alter the expression of the receptor or GIP. A sequence complementary to the mRNA transcript of the receptor protein gene normally found in the cell is made. This antisense RNA transcript of the inserted DNA can then base-pair with the normal mRNA transcript found in the cell and thereby prevent the MnRNA from being translated. It is of course necessary to select sequences of the 5' flanking region that are downstream from the transcriptional start sites for the receptor protein gene to ensure that the antisense RNA contains complementary sequences present on the mRNA.

Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zarnecnik et al., 1978 Proc. Natl. Acad. Sci. USA 75, 280–284; Zamecnik et al., 1986 Proc. Natl. Acad. Sci., 83, 4143–4146; Wickstrom et al., 1988 Proc. Natl. Acad. Sci. USA 85, 1028–1032; Crooke, 1993 FASEB J. 7, 533–539. Inhibition of expression of a gene by antisense oligonucleotides is possible if the antisense oligonucleotides contain modified nucleotides, see, e.g. Offensperger et al., 1993 EMBO J. 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 Proc. Natl. Acad. Sci. USA 85, 7079–7083 (synthesis of antisense oligonucleoside phosphoramidates and phosphorothioates to inhibit replication of human immnunodeficiency virus-1); Sarin et al., 1988 Proc. Natl. Acad. Sci. USA 85, 7448–7451 (synthesis of antisense methylphosphonate oligonucleotides); Shaw et al., 1991 Nucleic Acids Res 19, 747–750 (synthesis of 3' exonuclease-resistant oligonucleotides containing 3' terminal phosphoroamidate modifications); incorporated herein by reference).

The sequences of the 5' flanking region of receptor protein gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., 1989 Maher et al., Science 245, 725–730; Orson et al., 1991 Nucl. Acids Res. 19, 3435–3441; Postal et al., 1991 Proc. Natl. Acad. Sci. USA 88, 8227–8231; Cooney et al., 1988 Science 241, 456–459; Young et al., 1991 Proc. Natl. Acad. Sci. USA 88, 10023–10026; Duval-Valentin et al., 1992 Proc. Natl. Acad. Sci. USA 89, 504–508; 1992 Blume et al., Nucl. Acids Res. 20, 1777–1784; 1992 Grigoriev et al., J. Biol. Chem. 267, 3389–3395.

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Itakura et al., in Ann. Rev. Biochem. 1984 53, 323–356 phosphotriester and phosphitetriester methods); Narang et al., in Methods Enzymol., 65, 610–620 (1980) (phosphotriester method).

Preparation of GIP or GIP Receptor Protein Fragments

Compounds which are effective for altering binding or mimicking binding by GIP to the receptor can also consist of fragments of the receptor protein or GIP, expressed recombinantly and cleaved by enzymatic digest or expressed from a sequence encoding a peptide of less than the full length receptor protein or GIP. It is a routine matter to make appropriate receptor protein fragments, test for binding, and then utilize. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. Synthetic amino acid peptides can be prepared by phase synthesis described by J. Merrifield, 1963 J Am. Chem. Soc. 85, 2149, used in U.S. Pat. No. 4,792,525, and described in U.S. Pat. No. 4,244, 946, wherein a protected alpha-amino acid is coupled to a suitable resin, to initiate synthesis of a peptide starting from the C-terminus of the peptide. Other methods of synthesis are described in U.S. Pat. No. 4,305,872 and 4,316,891. The peptide can also be administered as a pharmaceutically acceptable acid- or base- addition salt, formed by reaction with inorganic acids such as hydrochloric acid, hydrobromic acid, perchloric acid, nitric acid, thiocyanic acid, sulfiric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

Preparation of blocking Antibodies

Figure 6:
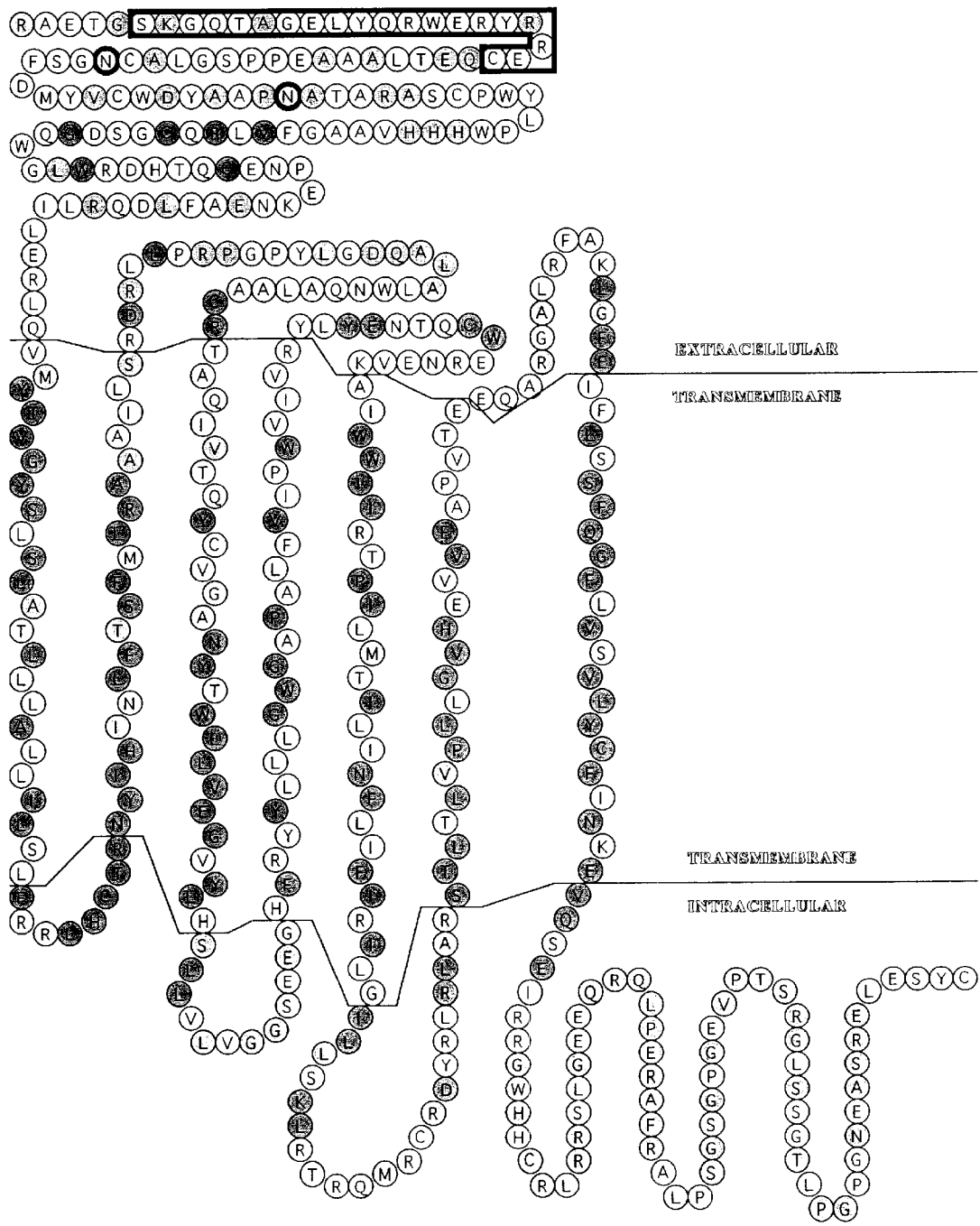
FIG. 6 is a schematic of the structure of the GIP receptor, with the region used to making antibodies blocking GIP receptor activation circled (SEQ ID NO. 1).

Antibodies to the GIP receptor can also be used to alter or regulate binding of GIP to its receptor; anti-idiotypic antibodies can be used to mimic the peptide. Blocking antibodies made to the N-terminal region of the GIP receptor circled in FIG. 6 are useful as inhibitors of GIP receptor activation. Antibodies can be polyclonal, monoclonal, fragments which have retained their binding specificity, and recombinant fragments. Humanized antibodies can be prepared using standard methods known to those skilled in the art.

Antibodies are generated by standard techniques, using human or animal receptor proteins. Antibodies are typically generated by immunization of an animal using an adjuvant such as Freund's adjuvant in combination with an immunogenic amount of the protein administered over a period of weeks in two to three week intervals, then isolated from the serum, or used to make hybridomas which express the antibodies in culture. Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes. These "humanized" antibodies present a lesser xenographic rejection stimulus when introduced to a human recipient.

The CDR grafting method described by Daugherty, et al., (1991) Nucl. Acids Res., 19:2471–2476, incorporated herein by reference, may be used to humanize a selected mouse monoclonal antibody. Briefly, the variable region DNA of a selected animal recombinant anti-idiotypic ScFv is sequenced by the method of Clackson, T., et al., (1991) Nature, 352:624–688, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

Formulations

Therapeutic compositions can be prepared by formulating the GIP for administration by injection, either intravenously, intramuscularly, or subcutaneously, in an appropriate carrier such as a phosphate buffered saline, or a controlled release formulation, for example, microparticles or gels, which release GIP over a period of time. In a preferred formulation for oral delivery, the peptide or peptide analog is administered in a capsule, tablet or other enteric coated formulation for delivery to the intestine, where it is released. Many controlled release formulations are known, for example, where drug is encapsulated using known techniques such as spray drying, solvent evaporation, or emulsification, in a polymeric material such as cellulose, polyhydroxy acids such as poly(lactic acid)-poly(glycolic acid), or non-biodegradable materials such as ethylene vinyl acetate or silicon. A review of methods to make liposomes is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214. GIP can also be administered topically, by inhalation, or administration to a mucosal surface (nasally, rectally, or vaginally), or by means of a transdermal patch.

Therapeutic Applications

The examples show that GIP receptors are present in bone cells including osteoblasts and osteocytes in bone proper, as well as in osteoblast-like osteosarcoma cell lines. These cell lines respond to GIP at physiological levels with metabolic responses exhibited by differentiated bone cells—collagen synthesis and alkaline phosphatase activity. The results indicate that GIP can be used to coordinate nutrient intake in the intestine with nutrient disposal in a variety of peripheral tissues including bone. The simplest explanation for the anabolic effects of GIP on bone cells in vitro would be that GIP increases cAMP (like PTH and PGE2) and this stimulates IGF-1 release, which then stimulates bone formation. The in vivo effects could be related to GIP-stimulated insulin and amylin secretion, which in turn stimulate bone formation. The simplest explanation for the antiresorptive effects is that GIP inhibits Il-6 secretion increased by either PTH or the hypogonadal state.

Undoubtedly, insulin and amylin contribute to GIP's action on bone, however the fact that GIP receptors in bone cells are of higher affinity and of greater quantity than those present in other tissues, such as the pancreas suggests that bone is a highly specific target of GIP action. The fact that GIP increases alkaline phosphatase activity (see preliminary results section) in a preosteoblastic cell line suggests that GIP may play a role in differentiation of the osteoblastic precursors. As noted above osteoblastic precursor cells (fibroblast CFU) can develop into muscle cells, osteoblasts, chondrocytes or adipocytes. The latter three cell types all express GIP receptors. Thus, it is hypothesized that GIP plays a role in osteoblastic differentiation, maturation and function and that GIP acts in concert with PTH in regulating bone matrix synthesis.

The compositions described herein can be used to treat or prevent osteoporosis. Osteoporosis is a disease characterized by an imbalance between bone formation and breakdown leading to a decrease in bone mass. Aging is associated predominantly with a decrease in bone formation, rather than bone loss, and the resulting net bone loss is associated with an increased risk of fractures. The patient population at the Veterans Medical Center is particularly at risk for osteoporosis. Since osteoporosis is more common in the postmenopausal woman, this disease in men has received less attention. However, aging men with lifestyle risk factors such as smoking and alcohol use and in men with associated illnesses such as chronic obstructive pulmonary disease, post kidney transplant and rheumatoid arthritis (on corticosteroids) are at a particularly high risk for developing osteoporosis. The resulting fractures associated with the osteoporosis are a major cause of morbidity, resulting in a decreased quality of life and a major expense for the medical center. Present therapy for osteoporosis is predominantly antiresorptive therapy, i.e. to prevent further bone breakdown and few medications (except for the soon to be released parathyroid hormone injection, perhaps estrogen in women and fluoride) are able to increase new bone formation.

Bone formation and growth is a complex process consisting of changes in bone diameter and shape. This process occurs through the sequential activation of two cell types: osteoclasts and osteoblasts. Osteoblasts are of mesenchymal origin derived from fibroblast colony forming units, as are chondrocytes, muscle cells and adipocytes. Osteoblasts are capable of secreting a number of factors (such as interleukins-6 and 11; MCS-F and GM-CSF) that can affect the development of osteoclasts. Osteoclasts develop from granulocyte-macrophage colony forming units and this development is modulated by a variety of factors, including interleukins 1, 3, 6 and 11. Recently, considerable interest has focused on interleukin-6 because its production from osteoblasts is stimulated by PTH and vitamin D and because of its possible involvement in several disease including primary hyperparathyroidism, multiple myeloma, rheumatoid arthritis, Paget's and hypogonadal osteoporosis. Interleukin-6 production from osteoblasts is regulated by sex-hormones (androgens and estrogens) which act on the Il-6 promoter. The role of Il-6 (in contrast to Il-11) in normal osteoclastic function is unclear but in certain pathologic states the Il-6 receptor is upregulated and Il-6 may then exert its effect. In bone cells derived from hypogonadal mice gp80, gp130 and Il-6 mRNA are all increased compared to normal cells. Thus, it is possible that Il-6 plays an important role in the accelerated bone loss associated with postmenopausal osteoporosis.

GIP is a unique peptide hormone in having receptors in both osteoblasts and osteoclasts (in contrast to PTH which has receptors only on osteoblasts). Thus, GIP provides an alternative therapy for the treatment of osteoporosis.

The GIP formulations are administered in an amount eliciting a therapeutic response, which can be measured using assays known to those skilled in the art, as demonstrated in the examples. In a preferred embodiment, GIP or analogues thereof, or compounds which increase the amount of endogenous GIP, is administered to women or men at risk of, or characterized by the symptoms of, osteoporosis, in an amount effective to increase type I collagen synthesis and/or bone density. Alternatively, GIP inhibitors can be used to promote bone absorption.

EXAMPLES

The present invention will be further understood by reference to the following non-limiting examples. To define the physiological role of GIP in normal bone metabolism four types of experiments were performed: 1) Studies on GIP receptor. A number of primary and transformed osteoblastic-like cells were examined for the presence of GIP receptors, a rabbit polyclonal antibody against the extracellular domain of the GIP receptor was generated and in initial studies both the antibody and the expression and location of GIPR in rat bone and osteoblastic like cells was characterized. 2) In vitro studies on GIP signaling pathways. The effect of GIP on cytosolic calcium and cAMP in cells was determined. 3) Studies on GIP action. GIP effects on osteoblastic collagen type I synthesis and alkaline phosphatase activity were examined. 4) Characterization of GIP action in vivo animal models: Experiments were performed to address the issue of what the physiological role of GIP is in vivo. Two models were utilized: an ovarectemized mouse that develops osteoporosis, and a transgenic mouse overexpressing GIP. In both models; GIP increased or maintained bone density.

The data demonstrates that GIP receptors are abundantly expressed in bone and bone derived cells and that GIP modulates the signal transduction events in these cells. The examples demonstrate that GIP receptors are present in normal rat bone, in osteoblasts and osteocytes, and in established osteoblast-like cell lines. The presence of these receptors in bone and osteoblast-derived cells was demonstrated in two ways: (1) mRNA for the GIP receptor was detected in cell lines and by in situ hybridization in osteoblasts and osteocytes in bone (data not shown) and (2) the protein was observed by both western blot analysis and indirect immunofluorescence in bone and in cell lines. Furthermore, the existence of GIP receptors in bone cells is specific, since a related receptor for another incretin hormone, glucagon-like peptide-1 (GLP-1), was not found. In addition, the receptors for GIP appear to be functional in that they bind the hormone with an affinity of approximately 0.5 nM, a value comparable to that seen previously in pancreatic β cells (0.3 to 30 nM depending on the cell system and the source of GIP (human versus porcine)). In addition, this binding affinity is in the physiological range of concentrations of GIP achieved in serum postprandially.

The functionality of the GIP receptors in osteoblast-derived cells was also demonstrated by their ability to couple to signal transduction pathways. Like other related seven transmembrane receptors, the GIP receptor in osteoblast-like cells appears to couple to both the cAMP and the phosphoinositide signalling pathways. In fact, the phosphoinositide response demonstrated greater potency in that a significant effect was observed at 0.1 nM GIP versus 1 nM for changes in cAMP content. The large increases in intracellular calcium concentration seen with the lower doses of GIP in osteoblast-like cells was unexpected based on previous studies with pancreatic β cell lines. Although GIP has been reported to increase extracellular calcium influx and to induce calcium mobilization from intracellular stores in pancreatic islets and cell lines, elevations in cAMP content have been considered the main intermediary in the incretin effect of GIP on glucose-induced insulin secretion.

The GIP receptors were also functional in that their occupation elicited cellular responses. Thus, treatment with GIP resulted in increased collagen type 1 mRNA expression and alkaline phosphatase activity with GIP concentrations as low as 0.1 nM, well within the physiological range. Changes in collagen type 1 expression required higher concentrations of GIP (greater than or equal to 1 nM), slightly above the normal physiological range.

In summary, in vitro studies demonstrate that GIP receptors are present in bone and bone-derived cells, and both in vitro and in vivo studies demonstrate that stimulation of these cells with GIP results in increases in intracellular calcium levels, cellular cAMP content, type 1 collagen expression, and alkaline phosphatase activity.

(1) Studies on GIP Action and its Receptor

These studies demonstrate that the GIP receptor is present in a variety of osteoblastic-like cells.

Example 1

Expression of GIP Receptors in Bone Cells

Expression of GIP receptor mRNA in sections of rat cuboideum and rat pancreas was screened for using in situ hybridization to an antisense digoxigenin-labeled GIP receptor probe on sections of cuboideum from adult Sprague Dawley rats. Background levels were measured as hybridization to a sense digoxigenin-labeled GIP receptor transcript in cuboidial osteocytes and progress zone. A 400 nucleotide digoxigenin-labeled RNA probe transcribed from a mouse GIP-receptor CDNA was used in the hybridization.

Methods and Materials

In brief, the rats were anesthetized, perfused with 4% paraformaldehyde and 0.2% glutaraldehyde transcardially. The cuboideum was harvested and fixed in 4% paraformaldehyde overnight at 4° C. The bones were decalcified in 10% EDTA for 4–6 days, dehydrated in ethanol and xylene and embedded in paraffin. 7 μm-thick sections were cut, deparaffined and rehydrated. The sections were treated with proteinase K and post-fixed in 4% paraformaldehyde. Hybridization was carried out at 70° C. overnight in solution containing 50% formamide, 5×SSC, 1% SDS, 5 mg/ml heparin and 50 mg/ml yeast tRNA. The post-hybridization washes were at 70° C. in 2×SSC, 1% SDS for 1 hour, 1×SSC, 1% SDS for 1 hour and 0.5×SSC, 1% SDS for 1 hour. The sections were incubated with alkaline phosphatase-conjugated anti-digoxigenin antibody for 2 hours and washed in PBS overnight. The color reaction was carried out in NBT and X-phosphate (Boehringer Mannheim). Positive staining results in blue color.

Results

GIP Receptor Message and Protein is Expressed by Osteoblasts

Receptor mRNA was detected in two human cultured osteoblastic cell lines, SaOS2, and MG63. Because mRNA expression does not always correlate with protein expression, the distribution of GIP receptor protein was evaluated. An affinity-purified polyclonal antibody to a peptide comprising part of the N-terminal extracellular domain of the human GIP receptor was generated and used to survey protein expression in a variety of cells and tissues by western blot analysis. As a positive control, a recombinant bacterially expressed protein corresponding to the amino terminus of the GIP receptor fused to GST was expressed.

Three osteoblastic-like cell lines (SaOS2, ROS 17/2.8 and MG63) contain a single immunoreactive band that corresponds to the predicted size of the GIP receptor. In contrast, two cell lines known not to contain the GIP receptor (Hela and NIH 3T3 fibroblasts) do not contain this immunoreactive band. Protein extracts from several tissues from a normal Sprague-Dawley rat were prepared and probed with the GIP receptor antibody by western blot. The same 50 kD immunoreactive band was observed in normal rat bone. In addition, the pancreas, brain and heart, tissues previously reported to contain the GIP receptor, were also positive, while the spleen, which has been reported not to contain the GIP receptor, did not contain any immunoreactive band, suggesting antibody specificity.

Four types of bone cells, osteoblasts, osteoclasts, osteocytes, and chondrocytes in the hypertrophic zone of the epiphyseal growth plate, were found to express GIP receptor transcripts by in situ hybridization. The receptor mRNA is expressed in two cultured osteoblastic cell lines, one of human (SaOS2) and the other of rat (ROS 17/2) origin, as well as in isolated rat osteoclasts. In contrast, message for receptors for glucagon-like peptide-1 (GLP-1), the other major "incretin" hormone, was not observed in this cell line, nor has its expression been reported in bone by others. R. V. Campos, et al., *Endocrinology* 134, 2156–2164 (1994). This hormone, like GIP, is secreted by endocrine cells in the small intestine, acts on the β-cell, and its receptor is a member of a subclass of seven transmembrane domain receptors that also includes parathyroid hormone, calcitonin, corticotrophin releasing factor, glucagon, pituitary adenylate cyclase activating polypeptide, vasoactive intestinal peptide, secretin and growth hormone releasing hormone.

Message levels for GIPR were 4.8 fold higher in MG63 cells vs. SaOS2 cells, consistent with the binding data.

Example 2

Immunofluorescent Studies of GIP Receptor Expression in Bone and Bonelike Cells

Because mRNA expression, identified by in situ hybridization, does not always correlate with protein expression, further studies using indirect immunofluorescence were carried out employing an antibody directed against an extracellular domain of the GIP receptor.

Distribution of GIP receptor immunofluorescence in sections of normal rat bone tibiae: and in SaOS2 cells was measured using a polyclonal antibody generated in rabbit to a synthetic oligopeptide corresponding to an extracellular region of the GIP receptor sequence (Animal Pharm Services, Inc., Healdsburg, Calif.). The antibody was affinity purified and specificity of the antibody was assessed by reacting with expressed GIP receptor protein. Background levels were measured as immunofluorescence in rat bone tibiae using only the CY3 labeled secondary antibody. Specificity of the primary antibody was also tested by competitively displacing the GIP receptor primary antibody binding m SaOS2 cells with primary antibody in the presence of an excess (140 µg) of the GIPR peptide antigen used as an antigen to generate the primary antibody. Sections of rat vertebrae were sectioned, fixed and probed with the GIPR antibody as the primary antibody, and then labelled with peroxidase. Similar patterns of expression were found in rat tibiae. SaOS2 cells grown in culture were also labeled with GIPR antibody. SaOS2 cells were incubated with primary antibody in the presence of an excess (140 µg) of the GIPR peptide antigen used as an antigen to generate the antibody. MG63 cells also were strongly positive with a labeling pattern similar to that of SaOS2 cells. Normal primary human osteoblasts were also examined for the GIPR.

Materials and Methods

Cell Culture

The cell lines studied in this report included SaOS2, MG63, ROS 17/2.8, Hela and NIH 3T3 fibroblasts. Normal primary human osteoblasts were also used (Clonetics, San Diego, Calif.). Cells were grown to confluence in MEM, RPMI or DMEM as appropriate (Bio Whittaker Inc., Walkersville, Md.), supplemented with 10% fetal calf serum (v:v) (HyClone Laboratories, Inc.; Logan, Utah), penicillin (100 U/ml), streptomycin (100 mg/ml), and amphotericin B (3 mg/ml), and utilized 3–7 days post confluence. For the studies on collagen type I expression, SaOS2 cells were grown in a glutamine- free medium, since we found that glutamine increased constitutive collagen expression levels.

Immunoblot Analyses:

A polyclonal antibody was generated in rabbit to a synthetic oligopeptide, SKGQTAGELYQRWERYRREC, corresponding to an extracellular region of the human GIP receptor protein sequence (amino acids 6–25 of SEQ ID NO:1), shown in FIG. 6. The oligopeptide was conjugated to KLH using an Imject maleimide activated immunogen conjugation kit (Pierce, Rockford, Ill.), and inoculated into rabbits (Animal Pharn Services, Inc., Healdsburg, Calif.). The serum was affinity purified on oligopeptide-BSA crosslinked to CNBr sepharose, and the antibody was assessed by western blot analysis to bacterially expressed GIP receptor protein. Specificity of the primary antibody was tested by competitively displacing the GIP receptor primary antibody binding in SaOS2 cells with primary antibody in the presence of an excess (140 µg) of the GIPR peptide antigen used to generate the primary antibody.

Indirect Immunofluorescence:

For the animal studies, three-month-old Sprague-Dawley rats (Charles River Laboratories, Wilmington, Mass.) were sacrificed and tissue removed. This protocol was approved by the Medical College of Georgia animal care committee (CAURE). Rats were anesthetized, perfused transcardially with 4% parafonnaldehyde and 0.2% glutaraldehyde. Tibiae and vertebrae were harvested and fixed in 4% paraformaldehyde overnight at 40° C. The bones were decalcified in 10% EDTA for 4–6 days, dehydrated in ethanol and xylene and embedded in paraffin. 7 µm-thick sections were cut, deparaffined and rehydrated.

SaOS2 and MG63 cells were plated on glass coverslips, grown in DMEM supplemented with 10% fetal calf serum for 48 hours and fixed in ice-cold 4% paraformaldehyde-PBS (PBS: 137 mM NaCl, 2.7 mM KCl, 8.1 mM $Na_2PO_4$, 1.15 mM $KH_2PO_4$, 1 mM $MgSO4$, pH 7.4) for 30 min. Cells were then rinsed 3×5 min in PBS and transferred into PBS+NH$_4$Cl (50 mM) for 15 min. After rinsing, the fields were covered with PBS+BSA (100 mg/10 ml) for 15 min (="blocking buffer"). The cells were then incubated with the GIP antibody in 500 μl PBS+BSA for 45 min. The cells were then rinsed and covered with secondary antibody, Cy3 goat-antimouse IgG (5 μl, Molecular Probes) and visualized by epifluorescence (Zeiss Axiophot microscope, Carl Zeiss Inc., Thornwood, N.Y.).

For the immunohistochemical localization, analyses were carried out using the Vectastain ABC peroxidase system with 3,3'-diaminobenzidine as the peroxidase substrate (Vector Laboratories, Burlingame, Calif.). Developed slides were dehydrated in ethanol, cleared in xylene, and counter-stained in Vector Hematoxylin.

Confluent bone cells (500,000/pair of lanes) were scraped into ice-cold phosphate-buffered saline (PBS, pH 7.4) and disrupted by sonication for 60 seconds in ice-cold homogenization buffer (60 mM Tris buffer, pH 7.4, 0.25 M sucrose, 10 mM EGTA, 2 mM EDTA, 10 mM β mercaptoethanol, and protease inhibitors). Proteins were placed in sample buffer (0.5 mM Tris, pH 6.8,4% SDS, 20% glycerol, 0.1% bromophenol blue) and boiled.

The denatured proteins were separated by sodium dodecyl sulfate-polyacrylamide gel electrophoresis (SDS-PAGE) and incubated with affinity-purified GIP receptor antibody at 1:250 dilution. Immunoreactive bands were visualized with a horseradish peroxidase-conjugated secondary goat anti-rabbit serum and developed with ECL (Pierce, Rockford, Ill.).

Results

In normal rat bone both osteocytes and osteoblasts demonstrated intense fluorescence. In contrast, rat bone did not demonstrate any cell labeling when incubated only with the CY-3 labeled antibody. SaOS2 cells also demonstrated intense non-nuclear fluorescence, which could be blocked by the presence of an excess of the antigen used to generate the antibody. This result indicates the specific binding of the antibody to the GIP receptor. MG63 cells also demonstrated intense fluorescence with a similar pattern to that of SaOS2 cells. As an additional control MG63 cells were labeled only with the secondary antibody demonstrating the specificity of the primary antibody.

Receptor protein expression was observed in all of the same bone cell types that express the receptor MnRNA. These studies show that the distribution of GIP receptors in bone is unique in the sense that receptors are present both on bone-resorbing ogteoclasts and bone-forming osteoblasts. In contrast, receptors for the two well-characterized peptide hormones known to act on bone, are present only on one of these bone cell types: the parathyroid hormone (PTH/PTHrP) receptor only on osteoblasts, A. Abou-Samra, et al., *Proc Natl Acad Sci USA* 89, 2732–6 (1992), and the calcitonin (CT) receptor only on osteoclasts. S. R. Golding, et al., *Horm Metab Res* 25, 477–80 (1993). Thus, one could predict that GIP would act simultaneously to stimulate bone formation and inhibit bone resorption.

2) In vitro studies on GIP Signaling Pathways:

Example 3

Effect of GIP on Cytosolic Calcium and cAMP

In pancreatic beta cells, where GIP receptors are known to be present, GIP is reported to increase intracellular calcium both by increases in calcium influx through voltage sensitive calcium channels and by mobilization from internal stores. In addition GIP increases cellular cAMP. Thus, even though both PTH and GIP have been reported to activate similar signaling pathways, PTH is anti-anabolic, while GIP appears to be anabolic to bone in vitro. In order to determine if the signaling pathways activated by GIP were different between pancreatic islet cells and bone cells, both calcium and cAMP responses were examined.

Materials and Methods

Intracellular Calcium Measurements with Fura-2:

Intracellular calcium measurements were made as described by Gasalla-Herraiz, et al., *Biochem Biophys Res Commun* 214:373–88 (1995). Briefly, SaOS2 cells were grown in 75 cm$^2$ flasks and removed by incubating in PBS/EGTA. Cells were loaded with the calcium sensitive dye fara-2AM in KRB, for 45 min at room temperature. The cells were then centrifuged and resuspended in KRB. After approximately 30 minutes at room temperature, to allow esterase cleavage of fura-2AM to fura-2, the cells were again centrifuged and placed in a cuvette in a dual-wavelength spectrophotometer (Photon Technologies International, South Brunswick, N.J.). Fluorescence was then measured using excitation wavelengths of 340 and 380 nm and an emission wavelength of 510 nm. Autoflourescence was measured in unloaded cells and this value subtracted from all the measurements.

Cyclic AMP Measurements:

cAMP measurements were done as described by Isales, et al., *Endocrinology* 129:489–95 (1991). Briefly, SaOS2 cells were grown to confluence in 60 mm$^2$ dishes and placed in KRB for 24 hours before use. In order to facilitate the measurement of cAMP production, 1 mM isomethylbutylxanthine (IBMX) was added prior to agonist addition for 10 minutes, followed by incubation with agonist for 10 minutes. Incubations were stopped by addition of 5% TCA, left on ice for 15 minutes and the cell extract collected. The extracts were neutralized by addition of a 1:1 solution ice cold Freon/Tri-N-octylamine (4:1,v/v). Each sample was vortexed for at least 30 sec to ensure adequate mixing. The mixture was then centrifaged at 2,500 rpm for 20 minutes (40° C.). The top aqueous phase containing the cAMP was collected. The pH of the upper phase was checked to ensure adequate neutralization. The samples were stored at –70° C. until analysis. cAMP was measured using a commercially available radioimmunoassay (Biomedical Technologies, Stoughton, Mass.). All incubations were performed in triplicate and each experiment was repeated three times using different cell preparations.

Results

GIP activates both cAMP and Ca$^{2+}$-Dependent Signal Transduction Pathways

To address the function of these GIP receptors in signal transduction, the signaling pathways normally engaged by the GIP receptor were examined initially. Receptors for GIP, like those for PTH, are members of a subclass of seven-transmembrane domain-spanning receptors that couple simultaneously to both adenylyl cyclase and phosphoinositide-specific phospholipase C (PI-PLC) signal transduction pathways.

Figure 1B:
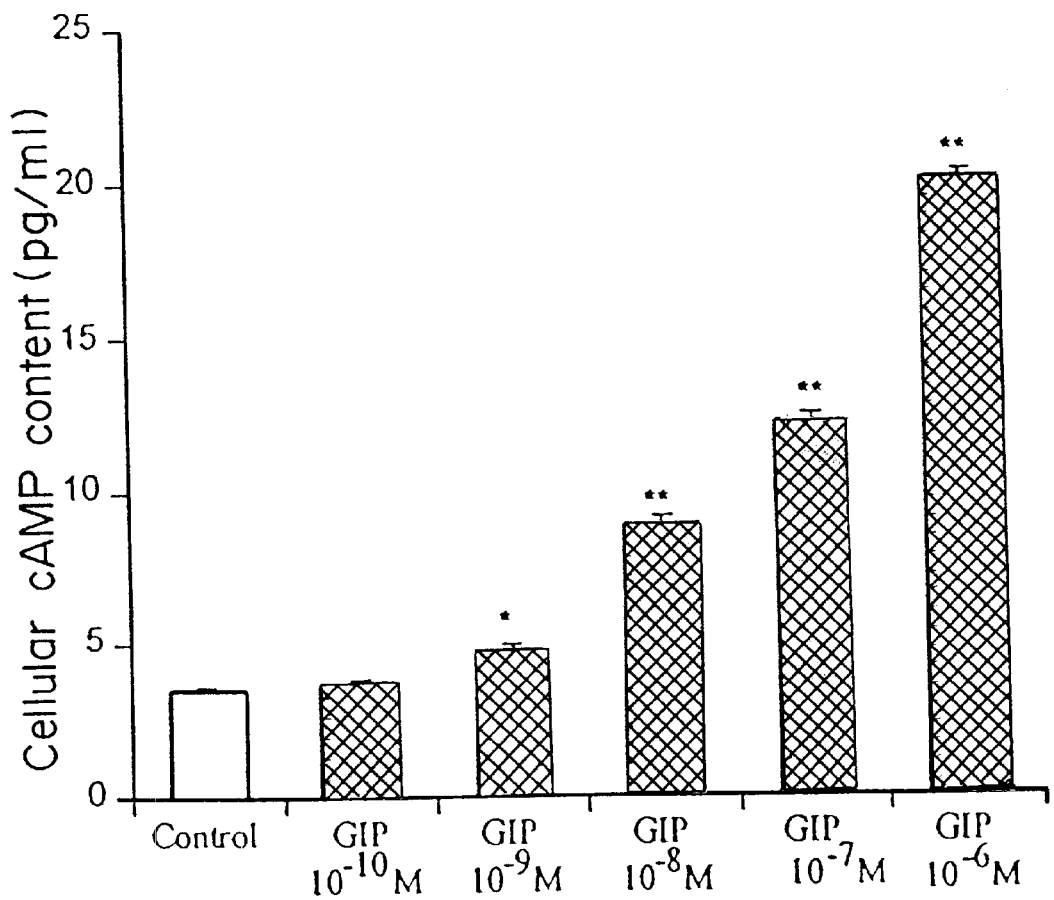

GIP increased both cytosolic calcium concentration and cellular cAMP content in SaOS2 cells as the calcium response shows a dose-dependent increase in [Ca$^{2+}$]i with a significant increase occurring at 0.1 nM GIP (FIG. 1A). GIP at concentrations of 1 nM and above was able to significantly stimulate elevations in cellular cAMP content (FIG. 1B). These elevations reached 710% above control at a GIP concentration of 1 uM.

The effect of GIP on cytosolic calcium concentration was determined first. GIP increases [Ca$^{2+}$]i in a dose dependent manner, with a significant increase occurring at 0.1 nM GIP, as shown by FIG. 1A. GIP at concentrations of 1 nM and above was able to significantly stimulate elevations in cellular cAMP content, as shown by FIG. 1B. These elevations reached 710% above control at a concentration of GIP of 1 µM. These higher concentrations of GIP are clearly pharmacologic and of unclear physiologic significance. However, the cellular responses observed in response to GIP serve to highlight the fact that these receptors are functional and linked to specific signal transduction pathways and able to elicit specific responses in these osteoblastic-like cells.

Example 4

Receptor Binding Studies

To further characterize the GIP receptors, binding of radiolabeled $^{125}$I-GIP to a variety of osteoblastic cell lines was examined. Receptor binding studies were performed as described by Orloff, et al., Endocrinology 137:5376–85 (1996). Briefly SaOS2, MG63 or NIH 3T3 fibroblasts were grown in 6 well plates and incubated with increasing concentrations of [$^{125}$I]-GIP (Amersham Pharmacia Biotech, Arlington Heights, Ill.) in the presence or absence of an excess of unlabelled GIP (1 µM) for two hours at room temperature. Cells were then washed 3x with 1 ml of cold PBS (+0.05% BSA) and solubilized with 0.3 M NaOH. The extract was counted in a gamma counter and background counts subtracted. Experiments were performed in triplicate.

The osteoblastic-like cell lines SaOS2 and MG63 displayed high affinity binding sites, whereas the 3T3 fibroblasts showed minimal background binding effects. Both MG63 and SaOS2 cells had similar $K_d$ values of approximately 0.3 nM, although the $B_{max}$ in MG63 cells was higher than that for SaOS2.

3) Studies on GIP Action

If GIP has an anabolic effect on bone mass, it must increase bone matrix synthesis. The major protein component of bone matrix is collagen type I. Thus, experiments were performed with SaOs2 in vitro to determine if GIP increased collagen type I synthesis Example 5

Studies on the Effects of GIP on Synthesis of Collagen

Materials and Methods

SaOs2 were grown in 75cm$^2$ flasks and stimulated with GIP at a dose of 0.1 uM, 1 nM, 10 nM or 100 nM for 24 hours (culture medium was replaced with fresh GIP containing medium every eight hours). After 24 hours, total RNA was extracted from cells using Trizol. RNA (20 µg) was electrophoresed on a 1.2% agarose-formaldehyde gel and transferred to a nylon filter. The blots were hybridized overnight at 65° C. with a $^{32}$P-labeled probe (10$^6$ cpm/ml), labeled by the random-priming method and washed at a maximum stringency. Blots were exposed to Kodak XAR 5 film and analyzed by densitometry, quantified on a Sun Sparc station using Bioimage software. (n=4, *=p<0.001). The collagen densitometry was normalized to GAPDH, a housekeeping gene, found not to change in response to GIP.

Results

Studies on the effects of GIP on cultured osteoblasts show that GIP, at a concentration of 1.0 nM or above, stimulates the synthesis of type 1 collagen, a marker for bone formation. GIP's effect on collagen type I was not dose-dependent. Rather, the lower GIP dose (0.1 nM) had no effect on collagen synthesis, while the higher doses (0.10, and 100 nM) had a maximal effect. Since collagen is the primary constituent of bone matrix, the ability to effect collagen synthesis is consistent with an anabolic effect on bone. GIP stimulates Collagen a (I) gene expression and activates alkaline phosphatase activity in osteoblast-like cells lines Having shown the GIP receptor is coupled to signaling events in bone cells, an issue still unanswered was the possible role of GIP in normal bone cell biology and its ability to induce a cellular response in vivo was unclear. To address this issue, the effect of GIP on two anabolic indices of bone formation: new matrix synthesis and alkaline phosphatase activity in osteblastic-like cells was examined.

Figure 2A:
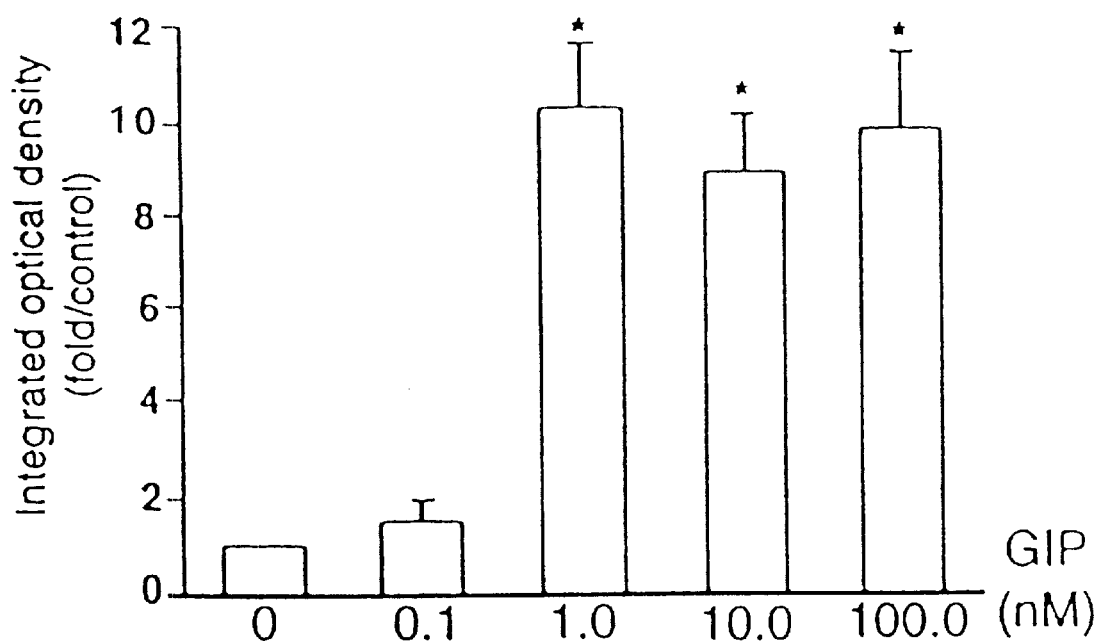
FIGS. 2A and 2B are graphs of the effect of GIP (0.1 nM, 1 nM, 10 nM and 100 nM) on collagen synthesis in cultured osteoblast-like cells. SaOs2 cells were grown in T75 flasks and stimulated with the indicated dose of GIP for 24 hours (culture medium was replaced with fresh GIP containing medium every eight hours). After 24 hourg, total RNA was extracted and probed with a collagen type I specific probe. The autoradiographs were then scanned and the densitometry quantified on a Sun Sparc station using Bioimage software. (n=4, *=p<0.001). The collagen densitometry was normalized to GAPDH, and shown as a function of GIP concentration in FIG. 2A.
Figure 2B:
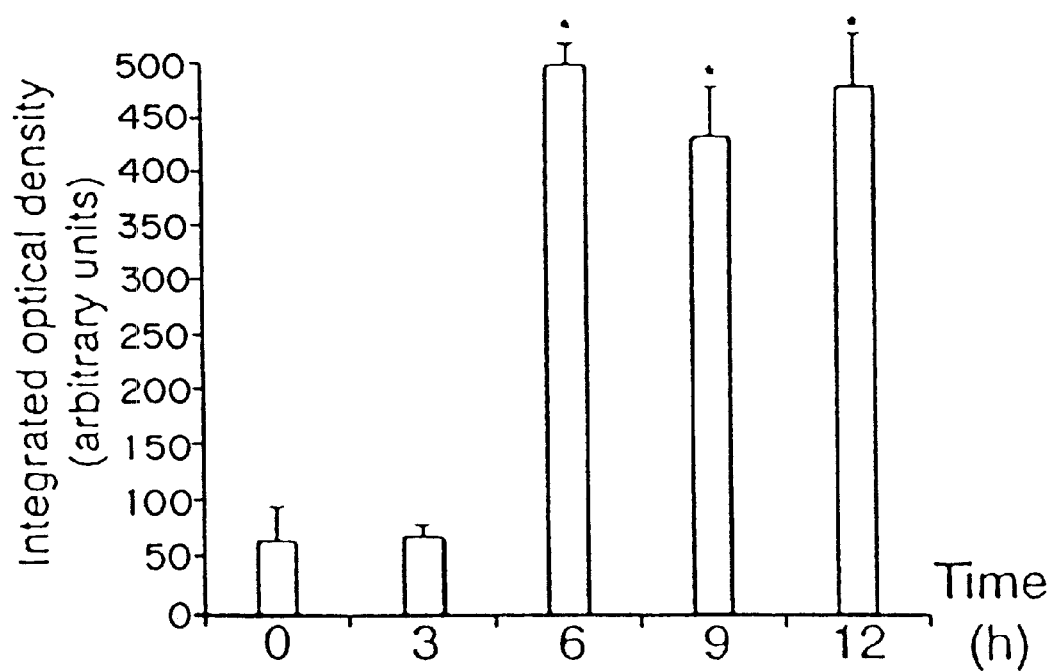

It was initially determined whether GIP could stimulate collagen type I expression in SaOS2 cells. SaOS2 cells were stimulated with increasing concentrations of GIP, and collagen type I expression was assessed by northern blot and quantitated by densitometry. GIP, at a concentration of 1 uM or above, stimulated the expression of type 1 collagen, a marker for bone formation, as shown by FIG. 2A. This GIP effect appeared to show a threshold effect, since no further increases in collagen type I expression were seen at the higher GIP concentrations. Since collagen is the primary constituent of bone matrix, the ability to effect collagen synthesis is consistent with an anabolic effect of GIP on bone. To examine this issue further, the time course of the GIP effect on collagen synthesis was assessed using the dose (1 nM) determined to be maximally effective in the previous experiment. The results are shown in FIG. 2B. The GIP effect on collagen mRNA could be observed after six hours of stimulation with no further increases observed at the later time points.

Example 6

Determination of Alkaline Phosphatase Activity

Osteoblasts follow an ordered pattern of development that is characterized by an initial proliferative phase (with increased expression of c-myc, c-fos, c-jun, histone and collagen type I) followed by a differentiation phase (with increased expression of alkaline phosphatase) and finally by a mineralization phase (with an increased expression of bone sialoprotein, osteopontin and osteocalcin). Accordingly, alkaline phosphatase activity is considered a sign of osteoblastic differentiation.

Methods and Materials

Preparation of RNA and Northern Blot Analysis:

Total RNA was extracted from cells using Trizol (Gaithersburg, Md.). RNA was stored at −70° C. until use. RNA (20 µg) was electrophoresed on a 1.2% agarose-formaldehyde gel and transferred to a nylon filter. The blots were hybridized overnight at 65° C. with a $^{32}$P-labeled probe (10$^6$ cpm/ml), labeled by the random-priming method and washed at maximum stringency. Hybridization was carried out in a solution of 7% SDS, 1% BSA, 1 mM EDTA, 250 mM Na$_2$HPO$_4$. The hybridized filters were washed with four 5 min washes of 2xSSC, 0.1% SDS at room temperature and twice in 0.1xSSC, 0.1% SDS for 30 min at 65° C. The blots were then exposed to Kodak XAR 5 film. The probes used were GAPDH (ATCC clone 57090), collagen 1 (i.m.a.g.e. clone# 308919) and a human GIPR fragment derived by PCR corresponding to transmembrane domains 2 to 7.

Alkaline Phosphatase Activity:

Alkaline phosphatase (ALP) activity was measured using a commercially available assay kit (ALP EC 3.1.1.1 Colorimetric test; Sigma Diagnostic, St. Louis, Mo.). This kit measures the conversion of p-nitrophenyl phosphate topnitrophenol and inorganic phosphate. The change in absorbance at 405 nm is directly proportional to ALP activity. MG 63 cells were grown in 6 well plates incubated with the indicated agonist for the indicated times (medium was changed daily with readdition of fresh agonist) and samples collected. The kit reagents were added to the sample cuvette in the spectrophotometer at 30° C. and absorbances at 405 nm obtained at 1, 2 and 3 minutes. ALP activity (U/L) was determined using the change in absorbance with time and a millimolar absorptivity of p-nitrophenol at 405 nm of 18.45.

Statistics:

Results are expressed as Means±SEM. Data were analyzed using either ANOVA or unpaired t-tests, where appropriate, with a commercial statistical package (lnstat, Graphpad Software Inc.; San Diego, Calif.).

Results

Figure 3:
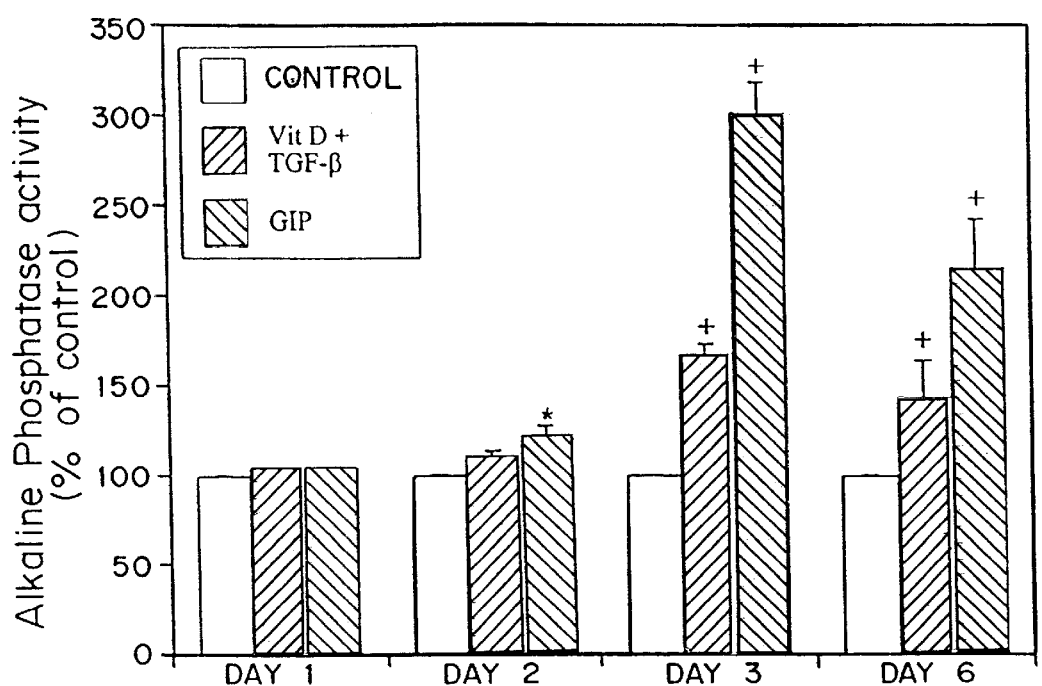
FIG. 3 is a graph of the effect of GIP on alkaline phosphatase activity in MG-63 cells grown to confluence in 6 well plates stimulated with GIP 0.1 nM for the indicated times (1, 2, 3 or 6 days) and the reaction stopped and alkaline phosphatase activity measured using a commercially available kit. The GIP effect on ALP was larger than that observed with 1,25 vitamin D (10ng/ml)+TGF-β10 ng/ml), used as a positive control. Shown are the Means±SEM of triplicates of four different experiments. *=p<0.05; +=p<0.001.

In addition to collagen type I synthesis, another index of anabolic activity in bone is alkaline phosphatase activity (ALP). This possibility was evaluated by determining the effect of GIP on alkaline phosphatase activity in the MG63 cell line. This cell line displays an abundance of GIP receptors by receptor binding studies. As shown in FIG. 3, GIP at a concentration of 0.1 nM significantly increased ALP activity as early as two days after stimulation and continued to increase ALP activity after 6 days of GIP exposure. Higher doses of GIP (1–10 nM) did not increase ALP activity any further than that found with 0.1 nM of GIP. The GIP effect on ALP was larger than that observed with 1,25 vitamin D (10 ng/ml)+TGF-β(10 ng/ml), used as a positive control. Hence, GIP is a potent inducer of alkaline phosphatase activity.

Example 7

Effect of GIP on Bone Resorption

Methods and Materials

Pregnant Sprague-Dawley rats (Charles River Laboratories, Kingston, N.Y.) were injected with 200 $\mu Ci^{45}Ca$ on day 18 of gestation and killed one day later to remove the labeled fetal radius and ulna. Bone explants were precultured for 24 h in BGJb medium, followed by 6 days of culture in BGJb with or without the substances to be tested (10 nM GIP; 10 nM PTH; and PTH with either 5, 10 or 50 nM GIP). Medium was changed every 3 days and $^{45}Ca$ was measured after every culture period. Resorption is expressed as the ratio of $^{45}Ca$ released from treated versus control bones.

Results

Figure 4:
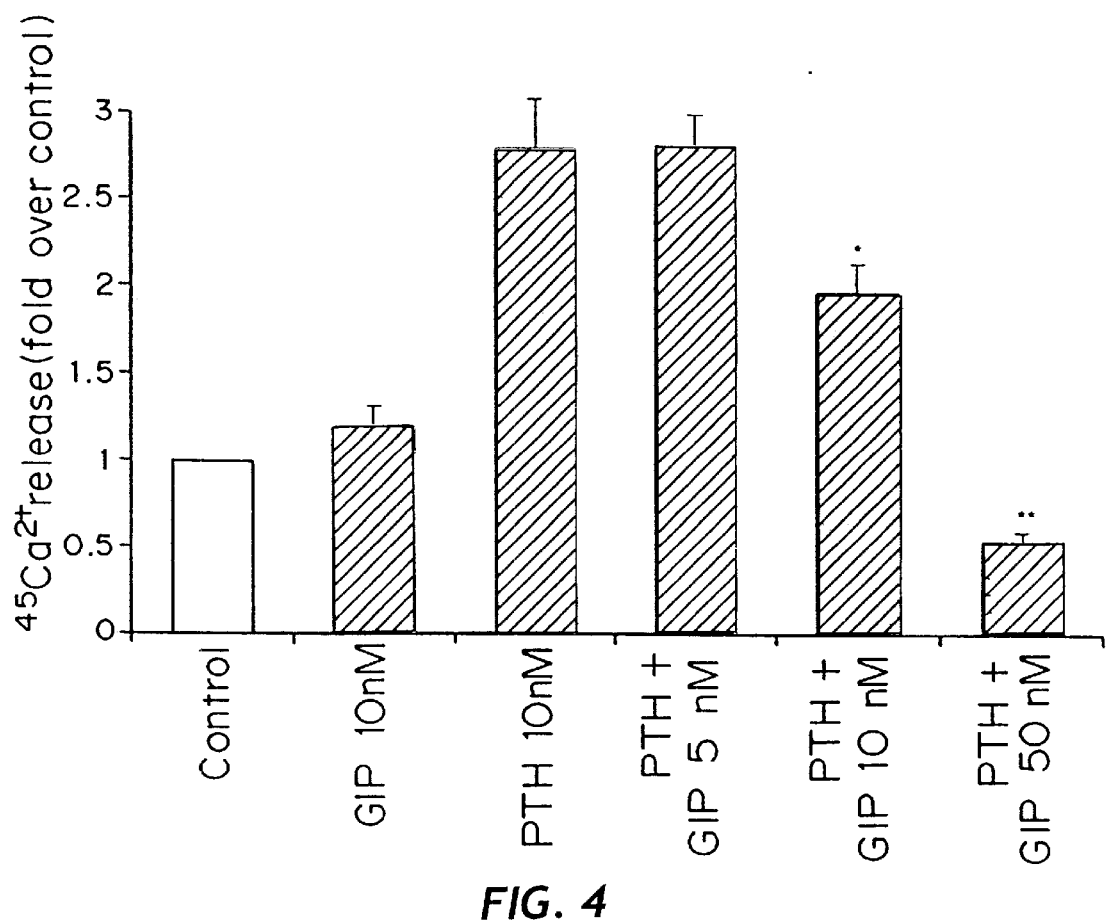
FIG. 4 is a graph of bone resorption ($^{45}Ca^{2+}$ release, fold over control) in cultured bone cells exposed to 10 nM GIP, 10 nM PTH, and the combination of PTH and GIP at three concentrations: 5 nM, 10 nM, and 50 nM.

The results are shown in FIG. 4. GIP inhibits PTH-induced bone resorption as measured in a fetal long bone assay system. Although the precise mechanism for PTH-induced bone resorption is unclear, the catabolic effect is at least partly operative.

4) Characterization of GIP Action in In Vivo Animal Models:

The data presented above suggests that GIP can modulate cellular function in vitro but does not demonstrate a physiological role for GIP in vivo. To address this issue two animal models were used: Sprague-Dawley rats receiving a daily GIP injection by tail vein and transgenic mice over-expressing GIP.

Example 8

Effect of GIP on Vertebral Bone Loss in Young Ovariectomized Rats

Since the ovariectomized (OVX) rat has been used extensively as an animal model for postmenopausal osteoporosis, this model was used to investigate the effects of GIP in vivo on bone formation.

Methods and Materials

Thirteen virgin female OVX and eleven virgin non-OVX Sprague-Dawley rats (150–174 g.), age 8 weeks, were purchased from Harlan Sprague-Dawley, Inc. (Indianapolis, Ind.), and maintained at the Animal Research Facility of the Medical College of Georgia. The protocol was approved by the CAURE Committee at the Medical College of Georgia. They were housed in separate hanging cages in a room maintained at 21 degrees Celsius, with 12 hr. light/ dark cycle at 0600/1800 E.S.T. They were fed ad libitum on a normal commercial pellet diet, Teklab Rodent diet (1.46% calcium) and had free access to water.

The rats were randomly divided into four weight matched experimental groups and selected to receive saline or human GIP (Bachem Inc. Torrance, Calif.) injections into the tail vein every morning. The rats were divided into the four study groups as follows:

1. Control. Five non-OVX rats received daily injections at the same time everyday (09:00) of saline vehicle for six weeks into the tail vein.
2. Control+GIP. Six non-OVX rats received daily injections of GIP (0.05 mg/kg) for six weeks into the tail vein as above.
3. OVX. Six OVX rats received saline vehicle injected daily for six weeks.
4. OVX+GIP. Seven OVX rats received daily injections of GIP (0.05 mg/kg) for six weeks into the tail vein.

The dose of GIP chosen is approximately equivalent to 10nM, a dose which gave near-maximal effects on stimulating collagen synthesis in vitro. The rats were weighed daily with length measured at baseline and again at 6 wks. Dual energy x-ray absorptiometry (DXA) using a Hologic QDR 1000/W, (Waltham, Mass.) was performed on all animals prior to initiation of treatment at 6 wks, and data was analyzed using the software Rat Whole Body version 5.53. At the end of the study the subjects were sacrificed and bone specimens taken for histomorphometric analysis and immunocytochemistry.

Results

Figure 5:
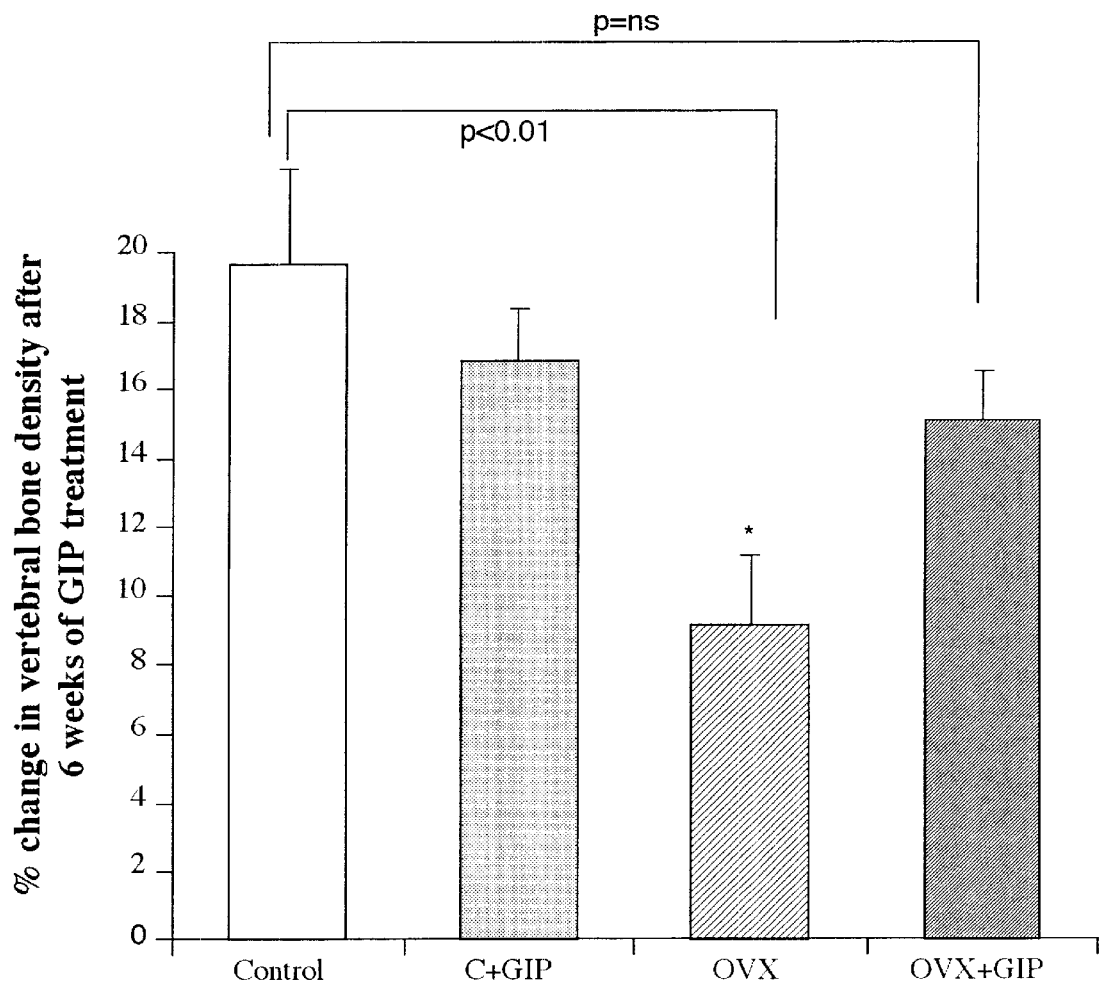
FIG. 5 is a graph of the percent change in vertebral bone density after six weeks of GIP treatment in ovarectomized virgin rats.

Bone densitometry, shown in FIG. 5, demonstrated a significant difference between the changes in bone mineral density (BMD) at the spine in the OVX group versus the Control and Control+GIP groups.

The OVX group had the lowest density of all groups. GIP attenuated the negative effects of ovariectomy on vertebral bone density. The OVX+GIP rats had mean six week vertebral BMD higher than the OVX rats (0.1434=/−0.0010 gms/cm2 vs. 0.1388+/−0.0045 gms/cm2 P=0.0385). Although the GIP treated control animals had a lower bone density than the untreated animals, this difference was not statistically significant. The reason why no increase in bone mineral density was observed in the GIP treated control group is not clear. It may relate to an inadequate GIP dose, timing of the injection (single versus multiple), age of the rats (young versus aged), duration of the experiment (6 weeks versus 8–12 weeks) or differences in the hormonal environment (i.e. increased PTH sensitivity).

Since GIP is an "incretin" hormone there was a concern about the possibility of making the animals hypoglycemic. Blood sugars were checked throughout the study and no statistically significant difference was found between those rats receiving GIP and those receiving saline.

In addition, there was a concern that if these animals were made hyperinsulinemic by GIP treatment that this would lead to inappropriate weight gain and that the weight gain itself might be responsible for increases in bone density. As reported by other investigators using the rat OVX model, these animals tend to gain weight; however GIP itself had no effect on weight. Baseline weights were: Control: 177.8±3.3; Control+GIP: 180.8±2.5; OVX: 178.7±4; OVX+ GIP: 186.0±2.7 (all expressed as the means of weight in grams±sem). Weights after six weeks of the experiment were: Control: 237.8±4.4; Control+GIP: 234.5±5.5; OVX: 294.7±6.2; OVX+GIP; 305.1±5.2 (all expressed as the means of weight in grams±sem)

The densitometry results shown in the figure are for trabecular bone. The software package utilized for the study did not permit analysis of specific sections of the extremities (i.e. proximal femur vs midshaft). The densitometry of the whole extremity was no different among the various experimental groups, GIP, like PTH, is a member of a subclass of seven transmembrane domain receptors that couple simultaneously to both adenylyl cyclase and phosphoinositide-specific phospholipase C (PI-PLC) signal transduction pathways. As shown by the earlier examples, GIP increases both cytosolic calcium concentration and cellular cAMP content in SaOS2 cells. GIP dose dependently stimulated increases in $[Ca^2+]i$ with a significant increase occurring at 0.1 nM GIP and GIP at concentrations of 1 nM and above was able to significantly stimulate elevations in cellular cAMP content. These elevations reached 710% above control at a GIP concentration of 1 $\mu$M. Based on these in vitro findings, the prediction would be that GIP would also be anabolic to bone in vivo. In fact, the studies in ovariectomized rats show that GIP administration prevents the loss of bone mass normally seen in these animals. All the rats increased their bone density, as expected in young rats which were still growing. However, the OVX group gained much less bone than controls (p<0.01). In contrast the OVX animals treated with GIP preserved their bone mass and their bone density was not statistically different from controls. This is evidence that GIP can be used to treat or prevent osteoporosis.

Example 8

Transgenic Mice

GIP Expressing Constructs In view of data that the GIP receptor can be downregulated by high doses of the peptide hormone, a construct that contained a regulatable promoter was designed. The regulatory elements associated with the mouse metallothionein promoter that have been characterized extensively in the laboratory of Dr. Richard Palmiter. Since the GIP peptide itself is under strict regulation, with secretion reported to occur only from duodenal K cells and from the salivary gland, and since improperly processed propeptides may generate circulating peptides that may antagonize the normal function of endogenous GIP, two expression constructs were designed. The first one incorporates the full-length prepropeptide, and the second secretes mature peptide that requires no processing. Thus, the former construct was designed to constitute the full-length GIP cDNA (preproGIP), and the latter was engineered to encode the GIP signal sequence appended to the mature GIP peptide (preMGIP). In order to test the potential of these constructs to generate biologically active GIP in established cell lines, the cDNAs were introduced into the expression vector pcDNA3, which incorporates the cytomegalovirus promoter and bovine growth hormone polyadenylation sites.

Figure 7:
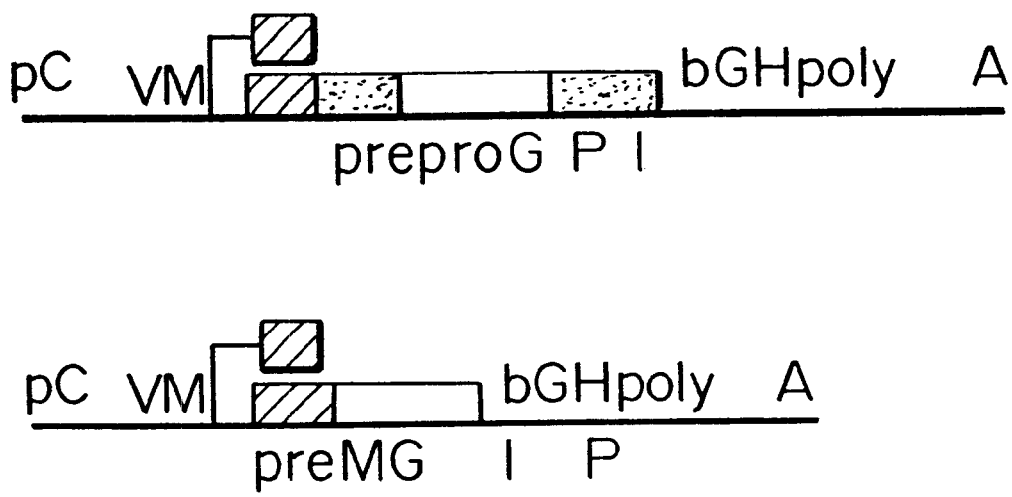
FIG. 7 is a schematic of GIP expression constructs. Both GIP cDNAs are expressed via transcriptional regulatory elements in vector pcDNA3. PreproGIP includes the entire coding sequence of the endogenous mouse GIP mRNA, while preMGIP is engineered to lack N- and C-terminal propeptide sequences.

These constructs are depicted schematically in FIG. 7. As shown in the Figure, both GIP cDNAs are expressed via transcriptional regulatory elements in vector pcDNA3. PreproGIP includes the entire coding sequence of the endogenous mouse GIP mRNA, while preMGIP is engineered to lack N- and C-terminal propeptide sequences.

Transfection of Cells in Culture with GIP Construct

Figure 8:
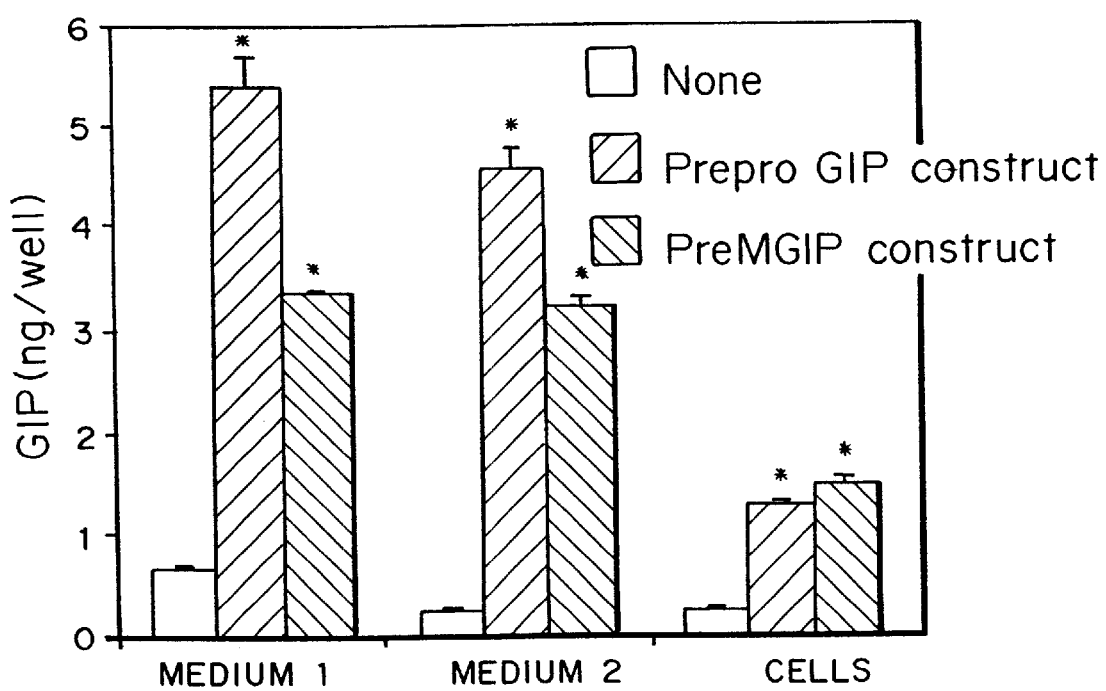
FIG. 8 is a graph of GIP secretion (ng/well) in transfected fibroblasts. NIH 3T3 fibroblasts were transfected using lipofectamine with the constructs depicted in FIG. 7, and with pEGFP as a control. Cells were grown to confluence, conditioned medium collected and GIP measured using a commercially available radioimmunoassay. Since it was possible that the GIP might not be secreted cellular content in cells collected and lysed was also measured. Shown are the means+SEM of three different measurements.

To assess the effectiveness of these two constructs, NIH-3T3 fibroblasts were transfected by liposome-mediated transfection (lipofectamine, GibcoBRL). Immunoreactive GIP secreted into the medium was measured on days 1 and 2 post-transfection by radioimmunoassay. To evaluate the efficiency of secretion, cellular contents were released by freeze-thaw lysis subsequent to supernatant removal on day 2 and evaluated for GIP immunoreactivity. GIP levels per well are reported in FIG. 8.

Figures 9A, 9B:
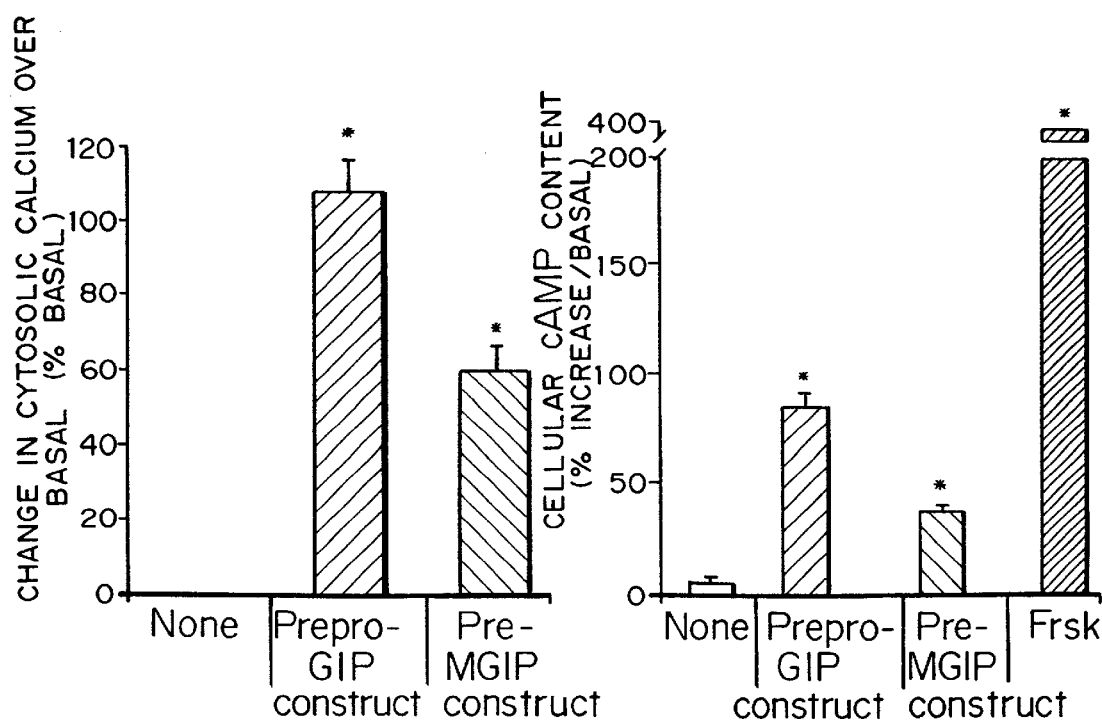
FIGS. 9A and 9B are graphs showing that transfection of GIP constructs leads to production of biologically active GIP. Fibroblast conditioned medium increases both intracellular calcium (FIG. 9A, change in cytosolic calcium over basal, % basal) and cellular cAMP content (FIG. 9B, cellular cAMP content, %increase/basal) in SaOS2 cells. 100 μl of fibroblast conditioned medium was added to SaOS2 cells and intracellular calcium measured using Fura-2. EFGP was used as a negative control for cytosolic calcium. Forskolin 10 μM was used as a positive control for cAMP. Shown are the means±SEM of triplicate measurements for each condition.

The constructs clearly produced immunologically detectable GIP. To assess the biological activity, the conditioned medium was added to SaOs2 cells and its effectiveness in elevating the two second messengers known to be stimulated by GIP: calcium and cAMP determined. The results are shown in FIG. 9A and 9B, respectively.

Production of Transgenic Mice Overexpressing GIP

Based on the transfection experiments described above, the full-length cDNA (preproGIP) was used to design a vector for generating GIP-overexpressing transgenic mice. A 500 bp mouse GIP cDNA was inserted into the unique NruI site of vector 2999. Vector 2999 incorporates the proximal mouse metallothionein I promoter upstream and human growth hormone polyadenylylation signals downstream of the introduced cDNA. This minigene is insulated by 17 kb of 5' and 3' regulatory sequences deriving from the genomic metallothionein locus to ensure tighter transcriptional regulation. The transgenic construct can be excised from the plasmid vector by flanking SalI sites. The mice were made using standard techniques for microinjection of DNA into the pronucleus of embryos, followed by implantation into pseudopregnant females.

Figure 10:
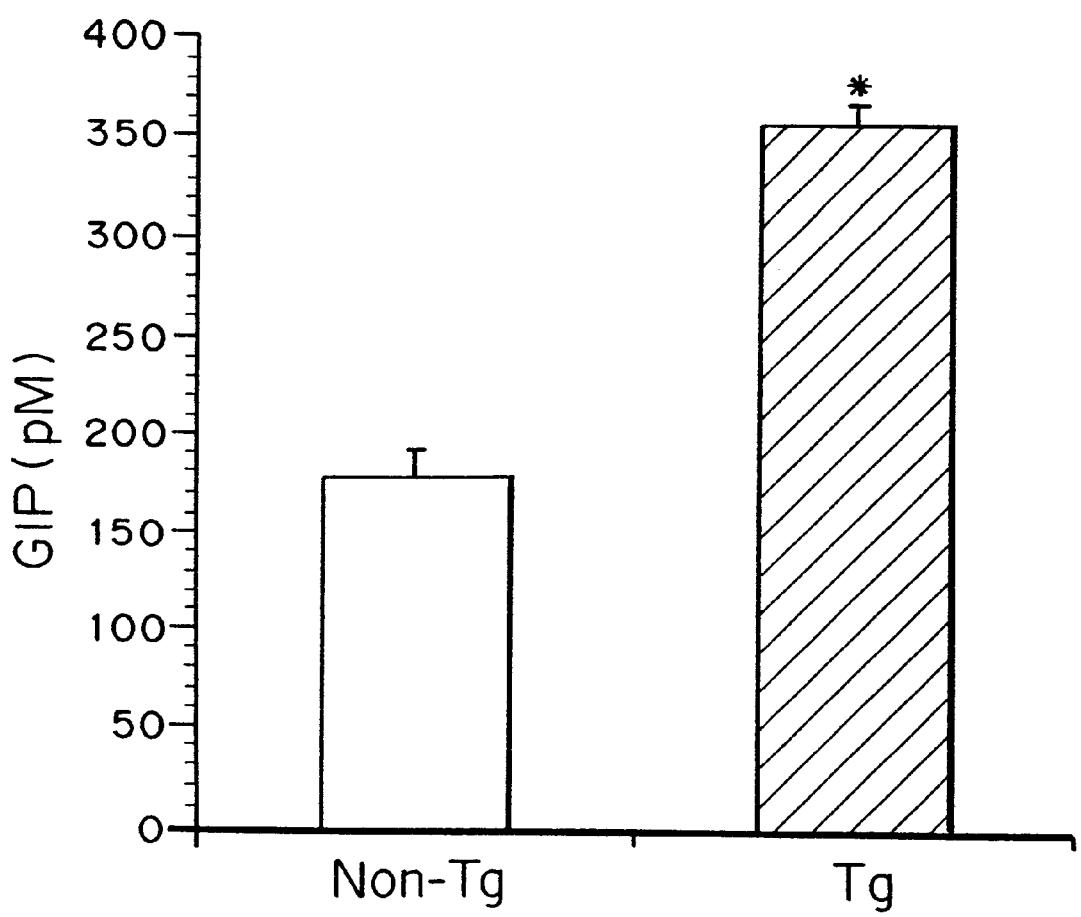
FIG. 10 is a graph of serum GIP levels in transgenic versus non transgenic mice. Approximately 50 μl of blood was drawn by eye bleed from both transgnic mice (Tg) and nontransgenic mice (NonTG) litter mates. GIP was measured using a commercially available radioimmunoassay (Peninsula laboratories, San Diego Calif.). Basal GIP levels in the transgenic are about two fold higher than nontransgenic prior to feeding them with a heavy metal.

Colonies of transgenic mice were established. Transgenic mice with a 10-fold increase in copy number have been selected and GIP levels measured (FIG. 10). An issue of major concern with these transgenic mice has been whether the high GIP levels would stimulate insulin release and lead to hypoglycemia and weight gain in these animals. However, these animals are not C different in their weight FIG. 11A). Nevertheless, the transgenic mice, even before stimulation with a heavy metal, have a significant increase in spinal bone mineral content (FIG. 11B). These results clearly demonstrate that GIP can be used to increase or maintain bone density.

Modifications of the methods and materials described herein will be obvious to those skilled in the art and are to be encompassed by the claims. The teachings of the references cited herein are specifically incorporated herein.

We claim:

1. A method for maintaining or increasing bone density or formation in a female subject having reduced bone mineralization associated with reduced ovarian function comprising administration of an effective amount of Glucose-Dependent Insulinotropic Peptide (GIP) as a pharmaceutically acceptable formulation to said subject, wherein said effective amount comprises sufficient GIP polypeptide to maintain or increase bone density in said subject.

2. The method of claim 1, wherein said reduced ovarian function is associated with menopause.

3. The method of claim 1, wherein said GIP polypeptide is administered intravenously.

4. The method of claim 1, wherein said GIP comprises GIP polypeptide expressed from recombinant GIP cDNA and isolated from cultured cells.

5. The method of claim 1, further comprising modifying said GIP polypeptide to increase the pharmacological half-life of the GIP.

6. A composition for maintaining or increasing bone density or formation in a female subject having reduced bone mineralization associated with reduced ovarian function comprsing an effective dose of Glucose-Dependent Insulinotropic Peptide (GIP) in a pharmaceutically acceptable carrier, wherein said effective dose comprises sufficient GIP polypeptide to increase serum GIP concentration by at least 0.001 nM to 100 μM.

7. The composition of claim 6, wherein said effective dose comprises from 0.0001 to 100 mg GIP per kg body weight of said subject.

8. The composition of claim 6, wherein said effective dose comprises from 0.001 to 5 mg GIP per kg body weight of said subject.

9. The composition of claim 6, wherein said effective dose comprises from 0.01 to 0.25 mg GIP per kg body weight of said subject.

10. The composition of claim 6, wherein said GIP comprises GIP polypeptide expressed from recombinant GIP cDNA and isolated from cultured cells.

11. The composition of claim 6, wherein said GIP polypeptide is modified to increase the pharmacological half-life of the GIP.

12. The composition of claim 6, wherein said pharmaceutical carrier is suitable for intravenous administration of GIP.

13. The composition of claim 6, wherein said reduced ovarian function is associated with menopause.

* * * * *

UNITED STATES PATENT AND TRADEMARK OFFICE
CERTIFICATE OF CORRECTION

PATENT NO.    : 6,410,508 B1
DATED         : June 25, 2002
INVENTOR(S)   : Carlos M. Isales et al.

It is certified that error appears in the above-identified patent and that said Letters Patent is hereby corrected as shown below:

<u>Title page,</u>
Insert -- Item [73] Assignee: Medical College of Georgia Research Institute, Inc., Augusta, GA-. --

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,410,508 B1
DATED          : June 25, 2002
INVENTOR(S)    : Carlos M. Isales, Roni J. Bollag and Howard Rasmussen It is certified that error appears in the above-identified patent and that said Letters Patent is hereby corrected as shown below:

Column 1,
Line 53, please correct the word "tun" to read -- turn --

Column 2,
Line 40, please correct the formula "cAMP apg/ml)" to read -- cAMP (pg/ml) --
Line 41, please correct the formula "[Ca2).+]$_i$" to read -- [Ca$^{2+}$]$_i$ --
Line 60, please correct the word "hourg" to read -- hour --

Figure 11A:
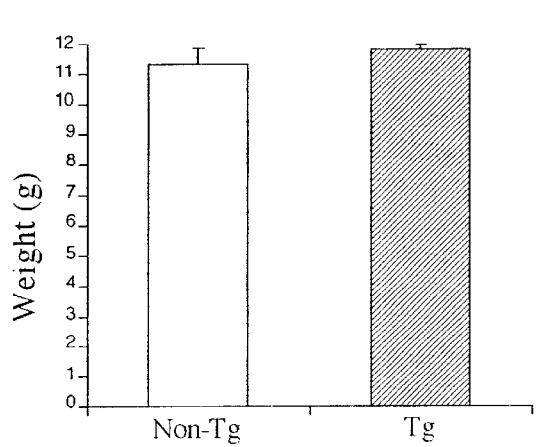
FIGS. 11A and 11B are graphs of transgenic GIP overexpressing mice: weight FIG. 11A, grams) and bone mineral density (FIG. 11B grams/cm²
Figure 11B:
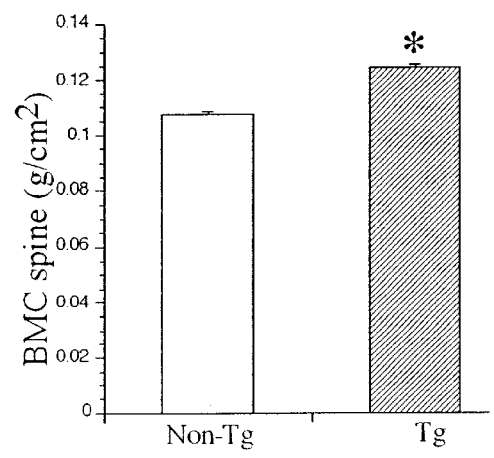

Column 3,
Line 61, please insert an opening parenthesis before the words "FIG. 11A, grams)" to read -- (FIG. 11A, grams) --
Line 62, please insert a closing parenthesis and period after the words "FIG. 11B grams/cm$^2$" to read -- (FIG. 11B grams/cm$^2$). --

Column 6,
Line 60, please correct the word "MnRNA" to read -- mRNA --

Column 7,
Line 5, please correct the spelling of the name "Zarnecnik" to read -- Zamecnik --

Column 11,
Line 44, please correct the word and punctuation of "models;" to read -- models, --

Column 12,
Lines 58 and 61, please delete the period after the Celsius symbol for "70° C." to read -- 70° C --

Column 13,
Line 61, please delete the colon after the words "tibiae: and" to read -- tibiae and --

Column 14,
Line 58, please correct the words "40° C." to read -- 4° C. --

Column 15,
Line 21, please correct the formula "pH 6.8,4% SDS" to read -- pH 6.8, 4% SDS --
Line 44, please correct the words "receptor MnRNA" to read -- receptor mRNA --
Line 47, please correct the word "ogteoclasts" to read -- osteoclasts --

Column 16,
Line 13, please correct the words "dye fara-2AM" to read -- dye fura-2AM --
Line 38, please correct the temperature "(40° C.)." to read -- (4° C). --

UNITED STATES PATENT AND TRADEMARK OFFICE
CERTIFICATE OF CORRECTION

PATENT NO. : 6,410,508 B1
DATED : June 25, 2002
INVENTOR(S) : Carlos M. Isales, Roni J. Bollag and Howard Rasmussen It is certified that error appears in the above-identified patent and that said Letters Patent is hereby corrected as shown below:

Column 17, Line 67 to Column 18, Line 1,
Please correct the words "doses (0.10, and 100nM)" to read
-- doses (1, 10, and 100 nM) --

Column 18,
Line 49, please delete the period after the words "at -70° C." to read -- at -70° C --
Line 53, please delete the period after the words "at 65° C." to read -- at 65° C --

Column 19,
Line 7, please delete the period after the words "at 30° C." to read -- at 30° C --

Column 22,
Line 56, please delete the "C" from the words "are not C different" to read
-- are not different --
Line 56, please insert an opening parenthesis before the words "FIG. 11A)." to read
-- (FIG 11A). --

Column 23,
Please correct the spacing of the 11th amino acid in each line of Sequence 1 to reflect the proper spacing; i.e., in the first line correct "A la" to read -- Ala -- ;
in the second line correct "G lu" to read -- Glu --;
in the third line correct "S er" to read -- Ser --;
in the fourth line correct "A la" to read -- Ala --;
in the fifth line correct "A la" to read -- Ala --;
in the sixth line correct "T rp" to read -- Trp --;
in the seventh line correct "L eu" to read -- Leu --;
in the eighth line correct "G ly" to read -- Gly --;
in the ninth line correct "S er" to read -- Ser --;
in the tenth line correct "L eu" to read -- Leu --;
in the eleventh line correct "A rg" to read -- Arg --;
in the twelfth line correct "L eu" to read -- Leu --;
in the thirteenth line correct "G In" to read -- Gln --;
in the fourteenth line correct "T yr" to read -- Tyr --;
in the fifteenth line correct "P he" to read -- Phe --;
in the sixteenth line correct "I le" to read -- Ile --;
in the seventeenth line correct "G lu" to read -- Glu --;
in the eighteenth line correct "L eu" to read -- Leu --;
in the nineteenth line correct "I le" to read -- Ile --;
in the twentieth line correct "A rg" to read -- Arg --;
in the twenty-first line correct "V al" to read -- Val --;
in the twenty-second line correct "A la" to read -- Ala --

UNITED STATES PATENT AND TRADEMARK OFFICE
CERTIFICATE OF CORRECTION

PATENT NO. : 6,410,508 B1
DATED : June 25, 2002
INVENTOR(S) : Carlos M. Isales, Roni J. Bollag and Howard Rasmussen It is certified that error appears in the above-identified patent and that said Letters Patent is hereby corrected as shown below:

<u>Column 25,</u>
Please correct the spacing of the 11$^{th}$ amino acid in each line of Sequence 1 to reflect the proper spacing; i.e., in the first line correct "G ln" to read -- Gln --;
in the second line correct "G ln" to read -- Gln --;
in the third line correct "L eu" to read -- Leu --;
in the fourth line correct "P ro" to read -- Pro --;
in the fifth line correct "S er" to read -- Ser --;
in the sixth line correct "S er" to read -- Ser --

Signed and Sealed this

Twenty-third Day of March, 2004

JON W. DUDAS
*Acting Director of the United States Patent and Trademark Office*